(12) United States Patent
Yang et al.

(10) Patent No.: US 9,234,004 B2
(45) Date of Patent: Jan. 12, 2016

(54) ANTIMICROBIAL PEPTIDES

(75) Inventors: Yi-Yan Yang, Singapore (SG); Nikken Wiradharma, Singapore (SG); Charlotte A. E. Hauser, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 112 days.

(21) Appl. No.: 13/882,320

(22) PCT Filed: Oct. 31, 2011

(86) PCT No.: PCT/SG2011/000385
§ 371 (c)(1),
(2), (4) Date: Apr. 29, 2013

(87) PCT Pub. No.: WO2012/057713
PCT Pub. Date: May 3, 2012

(65) Prior Publication Data
US 2013/0225481 A1 Aug. 29, 2013

(30) Foreign Application Priority Data

Oct. 29, 2010 (SG) .............................. 201008007-5

(51) Int. Cl.
*C07K 7/18* (2006.01)
*C07K 7/06* (2006.01)
(Continued)

(52) U.S. Cl.
CPC ... *C07K 7/08* (2013.01); *C07K 7/06* (2013.01); *C07K 14/00* (2013.01); *C07K 14/4723* (2013.01); *A61K 38/00* (2013.01)

(58) Field of Classification Search
CPC ......... C07K 14/4723; C07K 7/06; C07K 7/08
See application file for complete search history.

(56) References Cited

U.S. PATENT DOCUMENTS

2010/0016167 A1* 1/2010 Bardaji Rodriguez et al. .............................. 504/335

FOREIGN PATENT DOCUMENTS

EP 2062974 5/2009
JP EP 2062974 A1 * 5/2009 ............. C12N 15/09

OTHER PUBLICATIONS

Blondelle et al. Rapid identification of compounds with enhanced antimicrobial activity by using conformationally defined combinatorial libraries. Biochem. J. (1996) 313, 141-148.*

(Continued)

*Primary Examiner* — Karlheinz R Skowronek
*Assistant Examiner* — Jia-Hai Lee
(74) *Attorney, Agent, or Firm* — Wolf, Greenfield & Sacks, P.C.

(57) ABSTRACT

The present invention relates to antimicrobial peptides, to their use as antimicrobial agents and to their use in the treatment of (infectious) diseases, in particular infectious diseases caused by Gram-positive bacteria, Gram-negative bacteria, yeast or fungi. The present invention further relates to pharmaceutical compositions and kits comprising the antimicrobial peptides and to a method of lysing bacterial, yeast or fungal cells. The antimicrobial peptides consist of one of the following general formula: Wherein X is a hydrophobic amino acid, Y is a cationic amino acid, Z is an amino acid having a free thiol or thioether group, n is 2-4 and m is 0 or 1.

$$Z_m\text{—}(XXYY)_n\text{—}Z_m,$$

$$\begin{array}{c} Z_m\text{—}(XXYY \text{ or } YYXX)_n \\ \diagdown \\ KC \quad \text{and} \\ \diagup \\ Z_m\text{—}(XXYY \text{ or } YYXX)_n \end{array}$$

$$\begin{array}{c} Z_m\text{—}(XXYY \text{ or } YYXX)_n \qquad Z_m\text{—}(YYXX \text{ or } XXYY)_n \\ \diagdown \qquad \diagup \\ KC\text{—}CK \\ \diagup \qquad \diagdown \\ Z_m\text{—}(XXYY \text{ or } YYXX)_n \qquad Z_m\text{—}(YYXX \text{ or } XXYY)_n \end{array}$$

13 Claims, 32 Drawing Sheets

(51) Int. Cl.
*C07K 7/08* (2006.01)
*C07K 14/00* (2006.01)
*C07K 14/47* (2006.01)
*A61K 38/00* (2006.01)

(56) References Cited

OTHER PUBLICATIONS

Maget-Dana et al., Amphiphilic peptides as models for protein-membrane interactions: interfacial behavior of sequential Lys- and Leu-based peptides and their penetration into lipid monolayers. Supramolecular Science. 1997;4(3-4):365-8.

Maget-Dana et al., Comparative interaction of alpha-helical and beta-sheet amphiphilic isopeptides with phospholipid monolayers. Biopolymers. Jul. 2001;59(1):1-10.

Reynaud et al., Interactions of basic amphiphilic peptides with dimyristoylphosphatidylcholine small unilamellar vesicles: optical, NMR, and electron microscopy studies and conformational calculations. Biochemistry. May 18, 1993;32(19):4997-5008.

Wiradharma et al., Synthetic cationic amphiphilic α-helical peptides as antimicrobial agents. Biomaterials. Mar. 2001;32(8):2204-12. Epub Dec. 18, 2010.

Wiradharma et al., The effect of thiol functional group incorporation into cationic helical peptides on antimicrobial activities and spectra. Biomaterials. Dec. 2011;32(34):9100-8.

Yomogida et al., Involvement of cysteine residues in the biological activity of the active fragments of guinea pig neutrophil cationic peptides. Infect Immun. Jun. 1995;63(6):2344-6.

* cited by examiner

A

B

SEQUENCE LISTING

<160> NUMBER OF SEQ ID NOS: 20

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 1

Phe Phe Arg Arg Phe Phe Arg Arg
1               5

-continued

```
<210> SEQ ID NO 2
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: AMIDATION

<400> SEQUENCE: 2

Phe Phe Arg Arg Phe Phe Arg Arg Phe Phe Arg Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: AMIDATION

<400> SEQUENCE: 3

Ala Ala Arg Arg Ala Ala Arg Arg Ala Ala Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: AMIDATION

<400> SEQUENCE: 4

Leu Leu Arg Arg Leu Leu Arg Arg Leu Leu Arg Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (12)..(12)
<223> OTHER INFORMATION: AMIDATION

<400> SEQUENCE: 5

Leu Leu Lys Lys Leu Leu Lys Lys Leu Leu Lys Lys
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (16)..(16)
<223> OTHER INFORMATION: AMIDATION
```

```
<400> SEQUENCE: 6

Phe Phe Arg Arg Phe Phe Arg Arg Phe Phe Arg Arg Phe Phe Arg Arg
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (16)..(16)
<223> OTHER INFORMATION: AMIDATION

<400> SEQUENCE: 7

Leu Leu Arg Arg Leu Leu Arg Arg Leu Leu Arg Arg Leu Leu Arg Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (16)..(16)
<223> OTHER INFORMATION: AMIDATION

<400> SEQUENCE: 8

Leu Leu Lys Lys Leu Leu Lys Lys Leu Leu Lys Lys Leu Leu Lys Lys
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION

<400> SEQUENCE: 9

Leu Leu Lys Lys Leu Leu Lys Lys Cys
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 10

Cys Leu Leu Lys Lys Leu Leu Lys Lys Cys
1               5                   10

<210> SEQ ID NO 11
<211> LENGTH: 10
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION

<400> SEQUENCE: 11

Met Leu Leu Lys Lys Leu Leu Lys Lys Met
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (13)..(13)
<223> OTHER INFORMATION: AMIDATION

<400> SEQUENCE: 12

Leu Leu Lys Lys Leu Leu Lys Lys Leu Leu Lys Lys Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (14)..(14)
<223> OTHER INFORMATION: AMIDATION

<400> SEQUENCE: 13

Cys Leu Leu Lys Lys Leu Leu Lys Lys Leu Leu Lys Lys Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (14)..(14)
<223> OTHER INFORMATION: AMIDATION

<400> SEQUENCE: 14

Met Leu Leu Lys Lys Leu Leu Lys Lys Leu Leu Lys Lys Met
1               5                   10

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide

<400> SEQUENCE: 15

Phe Phe Arg Arg
1
```

```
<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Ala Ala Arg Arg
1

<210> SEQ ID NO 17
<211> LENGTH: 4
<212> TYPE: PRT
<213> ORGANISM: Artificial Sequence
<220> FEATURE:
<223> OTHER INFORMATION: Synthetic peptide

<400> SEQUENCE: 17

Leu Leu Arg Arg
1

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide

<400> SEQUENCE: 18

Leu Leu Lys Lys
1

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Leu Leu Lys Lys Leu Leu Lys Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is Cys or Met and may be absent
<220> FEATURE:
<221> NAME/KEY: misc_feature
<222> LOCATION: (2)..(3)
<223> OTHER INFORMATION: Xaa is Leu, Ile, Val or Phe
<220> FEATURE:
<221> NAME/KEY: misc_feature
<222> LOCATION: (4)..(5)
<223> OTHER INFORMATION: Xaa is Lys or Arg
<220> FEATURE:
<221> NAME/KEY: misc_feature
<222> LOCATION: (2)..(5)
<223> OTHER INFORMATION: is repeated 2, 3 or 4 times
<220> FEATURE:
<221> NAME/KEY: misc_feature
<222> LOCATION: (6)..(6)
<223> OTHER INFORMATION: Xaa is Cys or Met and may be absent
```

```
<220> FEATURE:
<221> NAME/KEY: MOD_RES
<222> LOCATION: (6)..(6)
<223> OTHER INFORMATION: AMIDATION

<400> SEQUENCE: 20

Xaa Xaa Xaa Xaa Xaa Xaa
1               5
```

ANTIMICROBIAL PEPTIDES

RELATED APPLICATION

This application is a national stage filing under 35 U.S.C. §371 of international application PCT/SG2011/000385, filed Oct. 31, 2011, the disclosure of which is incorporated by reference herein in its entirety.

The present invention relates to antimicrobial peptides, to their use as antimicrobial agents and to their use in the treatment of (infectious) diseases, in particular infectious diseases caused by Gram-positive bacteria, Gram-negative bacteria, yeast or fungi. The present invention further relates to pharmaceutical compositions and kits comprising the antimicrobial peptides and to a method of lysing bacterial, yeast or fungal cells.

Antimicrobial peptides (AMPs) secreted by the innate immune system of various organisms have been reported since three decades ago as the first form of natural defense against environmental parasitic infection [1]. To date, the primary structure of these peptides is so diverse that more than 1000 AMP sequences have been reported and documented in the AMP database [2]. Most of these peptides were derived from larger precursors [1], often empirically "optimized" by means of chemical modifications, such as glycosylation, fluorination, cyclization, or introduction of point amino acids mutations to tailor the biophysical properties of the natural AMPs. In addition, some peptides were also derived from a larger protein sequence through proteolysis, such as lactoferricin α-helical AMP from lactoferrin [3]. These derived AMPs often adopt different conformational structures in aqueous or membrane-like environments; however, they exhibit a certain degree of generalities, such as net cationic charge, amphiphilicity, primarily targeting the microbial cell membrane, and possessing antimicrobial activities through disruption and/or destabilization of the microbial cell membrane. Since most of these peptides, if not all, target the disruption of bacterial cell membranes in exerting their antimicrobial actions, it is suggested that AMPs can potentially escape the mechanisms involved in multidrug resistance, which is an increasingly difficult phenomenon faced as a result of repeated treatments with small molecular antibiotics [4]. Indeed, AMPs have been shown to be less susceptible to microbial resistance as compared to conventional small molecular antimicrobial agents [5]. Consequently, they are now widely accepted as blueprints for the development of new antimicrobial agents for the treatment of drug resistant infections.

Even though natural AMPs have shown to be useful in overcoming multidrug resistance, the development of such AMPs lacks in design principles and is not systematic. It mostly begins with a known natural peptide/short protein sequence, followed by modification and/or "optimization" to obtain improved antimicrobial effects, while reducing the undesirable cytotoxic effects towards mammalian cells. As such, this process becomes "random", involving "black box trial-and-error" procedures. In addition, the sequences of the peptides are often determined by the natural sequences, hence dictating the ease or difficulties of the peptide synthesis on resin. Moreover, there is an increasing argument recently that the clinical use of AMPs with sequences that are too close to those of human AMPs would inevitably compromise the natural defenses, possibly posing a threat to public health.

Accordingly, it was an object of the present invention to provide non-natural (or synthetic) peptides exhibiting antimicrobial activity, preferably with a broad spectrum and low minimum inhibitory concentrations (MICs). Furthermore, the peptides should be non-immunogenic and preferably have a selectivity towards microbial cell membranes, i.e. they should not induce significant rates of hemolysis when exposed to mammalian red blood cells.

The objects of the present invention are solved by a peptide having a general formula selected from the group consisting of

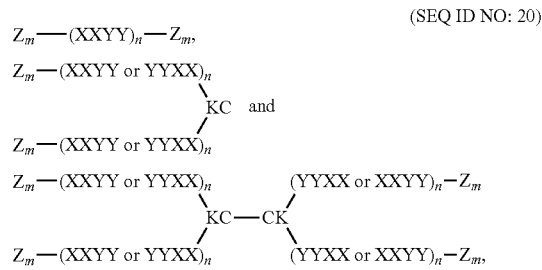

(SEQ ID NO: 20)

wherein

X is, at each occurrence, independently selected from an amino acid having a hydrophobic side chain;

Y is, at each occurrence, independently selected from an amino acid having a cationic side chain;

Z is an amino acid having a free thiol or thioether group;

n is an integer number between 2 and 4, preferably 2 or 3; and m is, at each occurrence, independently selected from 0 and 1.

The term "peptide", as used herein, is meant to refer to an isolated peptide.

The term "amino acid" includes naturally and non-naturally occurring L- and D-amino acids, peptidomimetic amino acids and non-standard amino acids that are not made by a standard cellular machinery or are only found in proteins after post-translational modification or as metabolic intermediates.

In one embodiment, X is selected from the group consisting of leucine (L), isoleucine (I), alanine (A), valine (V), phenylalanine (F), tryptophan (W) and methionine (M). In a preferred embodiment, X is selected from the group consisting of leucine (L) and phenylalanine (F). In a particularly preferred embodiment, X is leucine (L).

In one embodiment, said Y is selected from the group consisting of lysine (K) and arginine (R). In a preferred embodiment, Y is lysine (K).

In one embodiment, Z is selected from the group consisting of cysteine (C) and methionine (M).

In one embodiment, said peptide is selected from the group consisting of $(LLKK)_3$ (SEQ ID NO: 5), $(FFRR)_2$ (SEQ ID NO: 1), $(FFRR)_3$ (SEQ ID NO: 2), $(LLRR)_3$ (SEQ ID NO: 4), $(FFRR)_4$ (SEQ ID NO: 6), $(LLRR)_4$ (SEQ ID NO: 7), $(LLKK)_4$ (SEQ ID NO: 8), $(LLKK)_2C$ (SEQ ID NO: 9), $C(LLKK)_2C$ (SEQ ID NO: 10), $M(LLKK)_2M$ (SEQ ID NO: 11), $(LLKK)_3C$ (SEQ ID NO: 12), $C(LLKK)_3C$ (SEQ ID NO: 13) and $M(LLKK)_3M$ (SEQ ID NO: 14). In a preferred embodiment, said peptide is selected from the group consisting of $(FFRR)_2$ (SEQ ID NO: 1), $(FFRR)_3$ (SEQ ID NO: 2), $(LLRR)_3$ (SEQ ID NO: 4), $(LLKK)_3$ (SEQ ID NO: 5), $(LLKK)_2C$ (SEQ ID NO: 9), $C(LLKK)_2C$ (SEQ ID NO: 10), $M(LLKK)_2M$ (SEQ ID NO: 11), $(LLKK)_3C$ (SEQ ID NO: 13) and $M(LLKK)_3M$ (SEQ ID NO: 14).

In one embodiment, said peptide is selected from the group consisting of

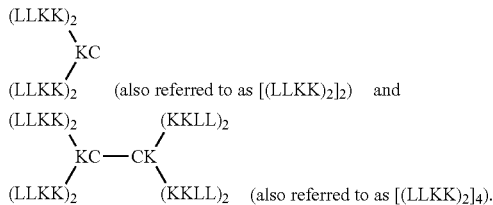

(also referred to as [(LLKK)₂]₂) and [(LLKK)₂]₄.

In one embodiment, the C-terminus/C-termini of said peptide is/are amidated. In one embodiment, the C-terminus/C-termini has/have the formula —CONHR, with R being selected from the group consisting of H, alkyl and substituted alkyl.

The objects of the present invention are also solved by a peptide as defined above for use as an antimicrobial agent.

The objects of the present invention are further solved by a peptide as defined above for use in a method of treatment of a disease.

In one embodiment, said disease is an infectious disease, wherein, preferably, said infectious disease is caused by Gram-positive bacteria, Gram-negative bacteria, yeast or fungi.

The objects of the present invention are also solved by a pharmaceutical composition comprising a peptide as defined above.

In one embodiment, said pharmaceutical composition further comprises at least one pharmaceutically acceptable carrier, diluent and/or excipient.

The objects of the present invention are also solved by a method of lysing a bacterial, yeast or fungal cell, said method comprising the step of exposing said cell to a peptide as defined above.

The objects of the present invention are further solved by a kit comprising a peptide as defined above.

The objects of the present invention are also solved by a method of treatment of an infectious disease, said method comprising the step of administering an effective amount of a peptide as defined above to a person in need thereof.

In one embodiment, said infectious disease is caused by Gram-positive bacteria, Gram-negative bacteria, yeast or fungi.

In one embodiment, said peptide is administered topically (e.g. in the form of an antimicrobial cream/paste). In another embodiment, said peptide is administered systemically.

The objects of the present invention are further solved by the use of a peptide as defined above for the manufacture of a medicament for the treatment of an infectious disease.

In one embodiment, said infectious disease is caused by Gram-positive bacteria, Gram-negative bacteria, yeast or fungi.

The present inventors expand the arsenal of the synthetic AMPs by using material design principles to mimic the α-helical structure of AMPs derived from the host defense immune system. The cationic amphiphilic peptides according to the present invention are designed based on the α-helical protein folding principles, whereby the peptide carbonyl O atom and amide proton between the $i^{th}$ and $(i+4)^{th}$ amino acid positions form a paired hydrogen bond, hence introducing a regular turn every 3.6 amino acids, and resulting in a folded structure known as the α-helical conformation. By garnering hydrophobic interactions between the side groups of the hydrophobic amino acids at the adjacent $i^{th}$ and $(i+4)^{th}$ positions after each turn, α-helical folding can be enhanced, when the amino acids selected do not belong to the helical breakers category. In order to ensure ordered structural interaction between side groups of amino acids at $i^{th}$ and $(i+4)^{th}$ positions, a repeat primary structure containing 4 amino acids is used when designing the AMPs. Furthermore, by providing the same cationic charge at the $(i+2)^{th}$ and $(i+3)^{th}$ positions of the peptide, repulsive forces arising from the same charge amino acid residues would help to make the peptide molecules unfold in solution, thereby mimicking the α-helical folding characteristics of the natural α-helical AMPs, which have been reported to form helical structures upon charge neutralization and/or interaction with bacterial membranes. This mimicry is ensured by keeping the cationic and hydrophobic content within the repeat units balanced (50/50 content), so that the long-range repulsive forces will overcome the short-range hydrophobic interactions, hence unfolding the peptide molecules in solution. As such, the resulting primary peptide structure can be simplified as repeat of a XXYY amino acid sequence, i.e. $(XXYY)_n$, whereby X is a hydrophobic amino acid, Y is a cationic amino acid, and n indicates the number of repeat units. Since the presence of zwitterionic moieties in antimicrobial agents reduces their effectiveness, the C-terminus of the peptides is preferably amidated in order to maintain the high net positive charge. Another factor that was also taken into consideration in designing these α-helical peptides is the selection of the amino acid residues, which will result in different propensity towards secondary structure formation. Phenylalanine (F) and arginine (R) are known to have indifferent propensity towards helical formation, while leucine (L) and lysine (K) residues are known to have strong propensity to form an α-helix conformation.

In addition to the helical formation principles, the design also takes into consideration the desired end-results of having high selectivity of the peptides towards microbial cells over mammalian red blood cells. In order to achieve this goal, two strategies are employed according to the present invention. The first strategy is to vary the number of repeat units (n) within the designed $(XXYY)_n$ peptide sequence in order to yield different facial amphiphilicity of the folded α-helical peptides. The second strategy is to introduce an amino acid having a free thiol group, e.g. a cysteine residue, at the termini of the peptide sequence, which can be used to further optimize/broaden the antimicrobial activities/spectrum of the synthetic peptides. Thus, first, the amino acid composition and number of repeat units are optimized (e.g. in terms of the hydrophobic/hydrophilic balance) in order to provide a better structural design of the α-helical peptides and improve the selectivity towards microbial cells, and then, the best sequences are modified with one or two cysteine or methionine residues at the peptide's C and/or N termini in order to enhance and/or broaden the antimicrobial activities and/or antimicrobial spectrum of the synthetic AMP.

The present inventors have found that synthetic α-helical AMPs with 3 repeat units, e.g. (FFRR)₃ (SEQ ID NO: 2), (LLRR)₃ (SEQ ID NO: 4), and (LLKK)₃ (SEQ ID NO: 5), are more selective towards microbial cells than towards rat red blood cells, with minimum inhibitory concentration (MIC) values that are more than 10 times lower than their 50% hemolytic concentrations (HC₅₀). They are effective against Gram-positive B. subtilis and yeast C. albicans; and the studies using scanning electron microscopy (SEM) have elucidated that these peptides possess membrane-lytic activities against microbial cells. The inventors have also found that incorporation of sulfhydryl/thiol- or thioether-containing amino acids widens the spectrum of the antimicrobial activity. With such incorporation, peptides with a shorter repeat unit (n=2) that are much less hemolytic, are effective to suppress the growth of Gram-positive *B. subtilis*, Gram-negative *E. coli* and *P. aeruginosa*, and yeast *C. albicans*, at a concentration that induce less than 10% hemolysis. Furthermore, non-specific immune stimulation assays of a typical peptide show negligible IFN-α and IFN-γ inductions in human peripheral blood mononuclear cells, which implies that they are non-immunogenic and safe for both systemic and topical use.

Taken together, the peptides according to the present invention can adopt an α-helical conformation in a simulated membrane environment. They exhibit a broad spectrum of antimicrobial activities against both Gram-positive and Gram-negative bacteria as well as yeast with low minimum inhibitory concentrations (MICs). At these concentrations, they do not induce significant hemolysis over mammalian red blood cells, indicating excellent selectivity towards microbial cell membranes. Therefore, these peptides are very promising antimicrobial agents against a broad variety of microbes.

The peptides according to the present invention are short and can be easily synthesized at relatively low cost. They can be used in a variety of applications in both medication and personal care, for example, they can be used as topical antimicrobial agents (e.g. in the form of an antimicrobial cream/paste), as systemic antibiotics, or coated onto a surface of a medical device that require anti-infective applications (such as a catheter).

The peptides according to the present invention can be used for lysing bacterial, yeast or fungal cells, e.g. in order to isolate (recombinant) proteins from bacterial, yeast or fungal cells. Conventional commercially available kits for bacterial protein extraction (e.g. EasyLyse Cat. No. RP03750, Ready-Lyse Cat. No. R1802M, R1804M, R1810M by Epicentre Biotechnologies) use lysozyme, a ~14 kDa protein obtained from chicken egg, for lysing the bacterial cells. The membrane-lytic peptides according to the present invention (~1-2.5 kDa) can be used as lysis component instead of lysozyme. The use of these peptides can facilitate the purification of the protein of interest, since the peptides are much smaller than most proteins.

Finally, the inventors have demonstrated that branching molecular design enhances antimicrobial activity and reduces undesired hemolysis, leading to better selectivity towards microbes over mammalian cells. This strategy can also be applied to optimize molecular structure of other types of macromolecular antimicrobials such as polymers.

Reference is now made to the figures, wherein

Figure 2:
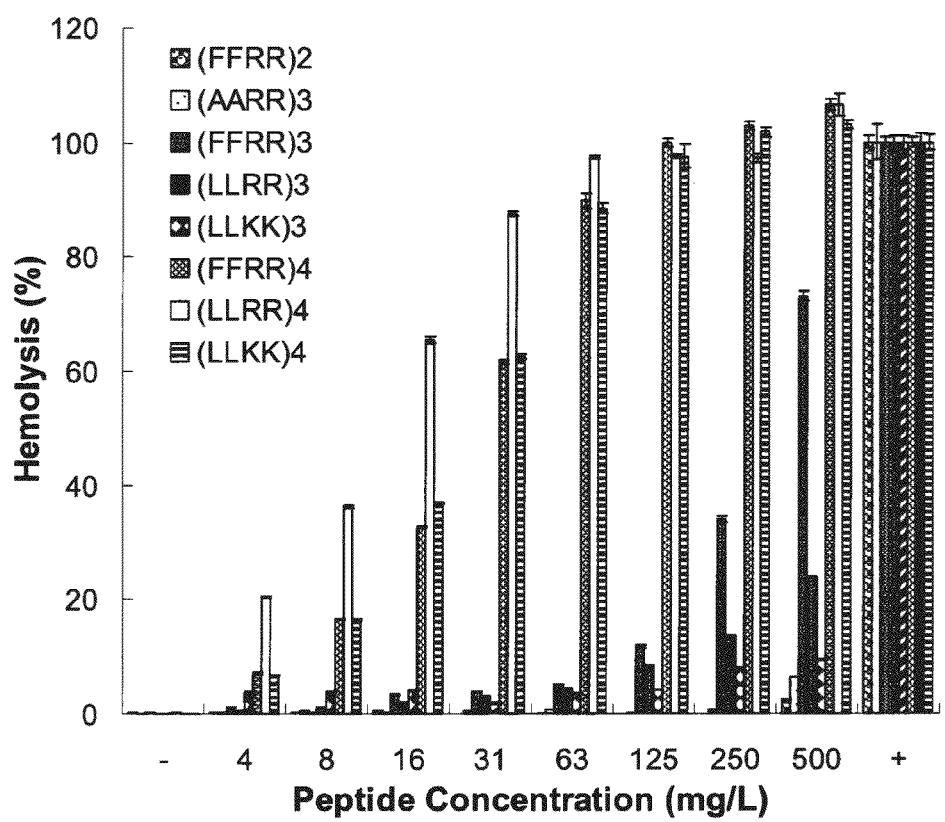
FIG. 2A shows the hemolytic properties of exemplary synthetic α-helical antimicrobial peptides (n=2-4 replicates) with PBS as negative control, and 0.1% Triton-X as positive control; SEQ ID NOs: 1, 3, 2, 4, 5, 6, 7 and 8 can be found in the legend from top to bottom, respectively.
Figure 2:
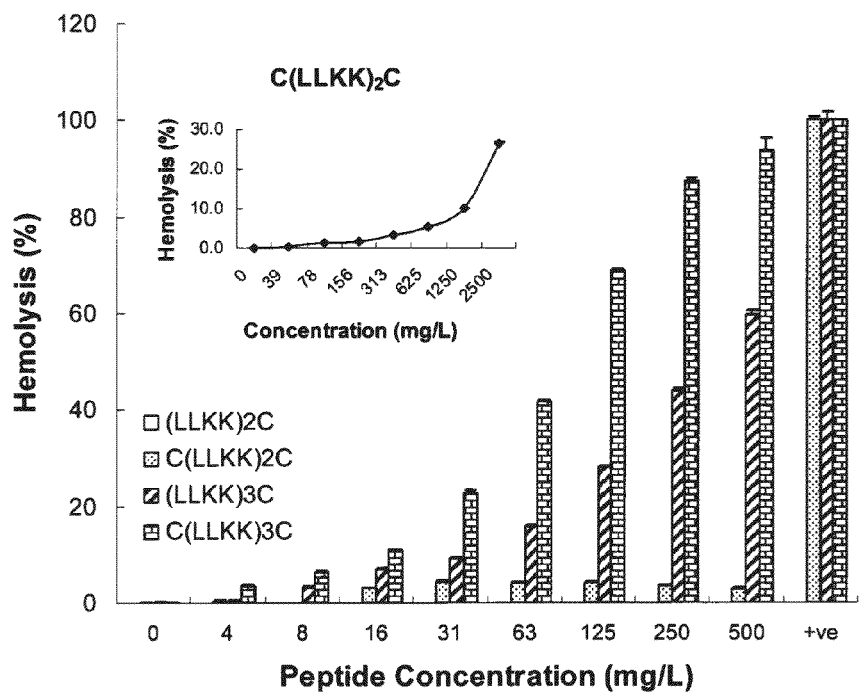

FIG. 2B shows the hemolytic properties of exemplary synthetic α-helical antimicrobial peptides using the sulfhydryl modification strategy (n=2-4 replicates) with PBS as negative control, and 0.1% Triton-X as positive control; SEQ ID NO: 10 can be found in the smaller graph. SEQ ID NOs: 9, 10, 12 and 13 can be found in the legend from top to bottom, respectively.

Figure 4:
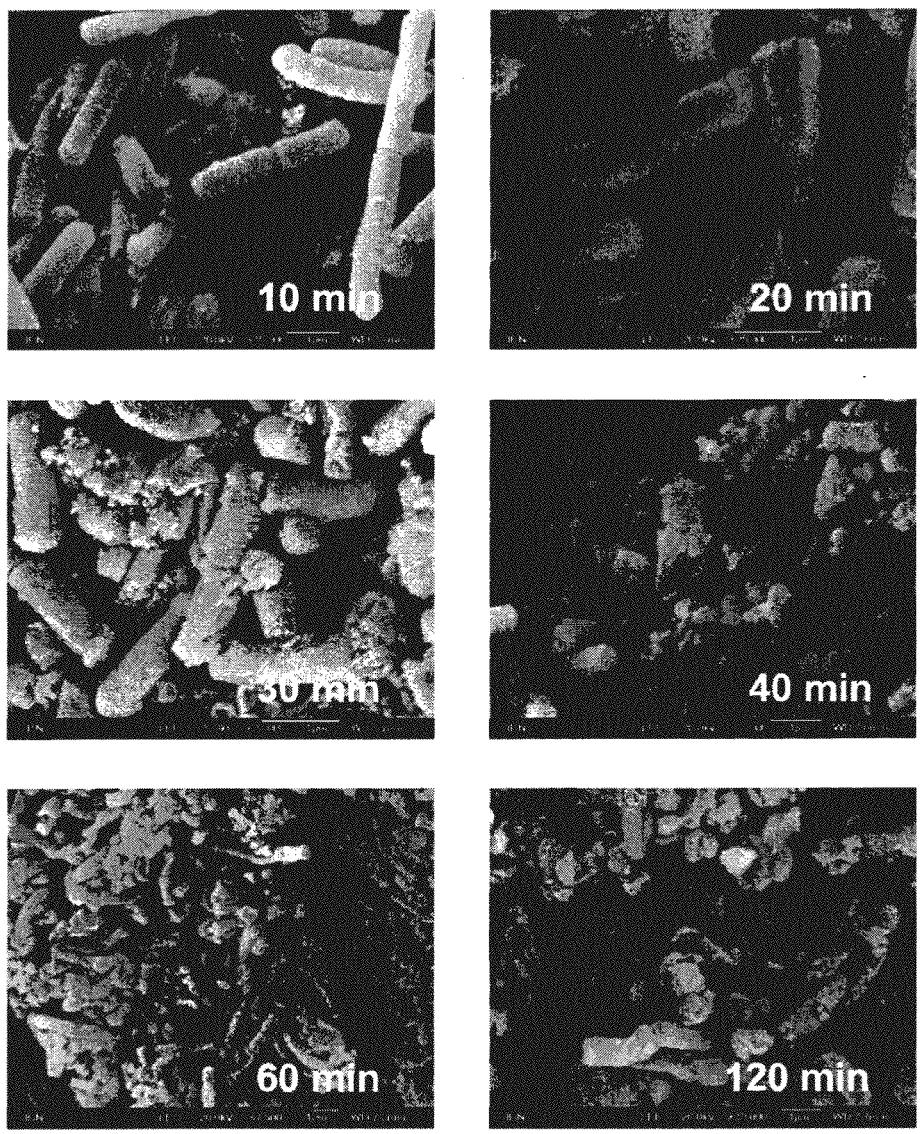
Figure 5:
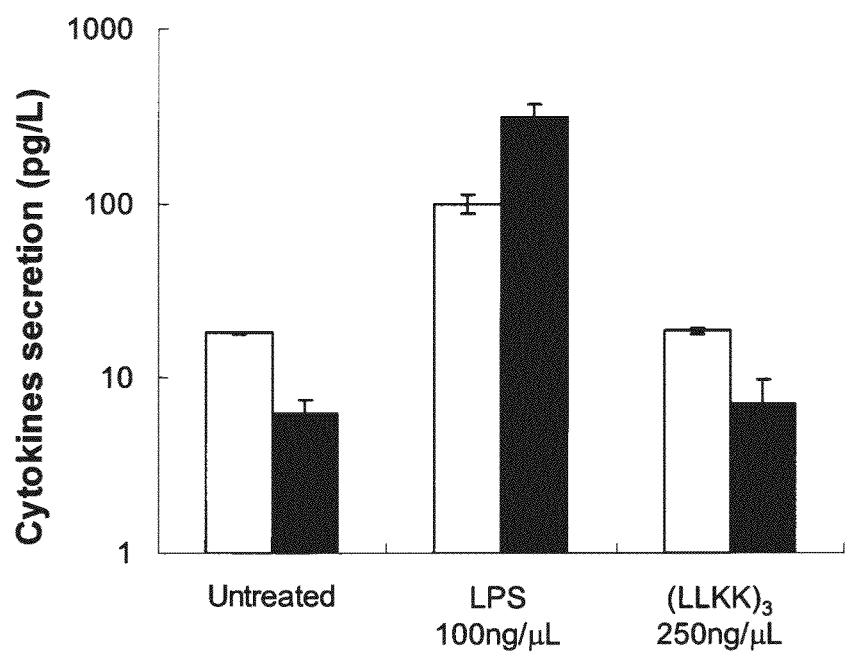
Figure 6:
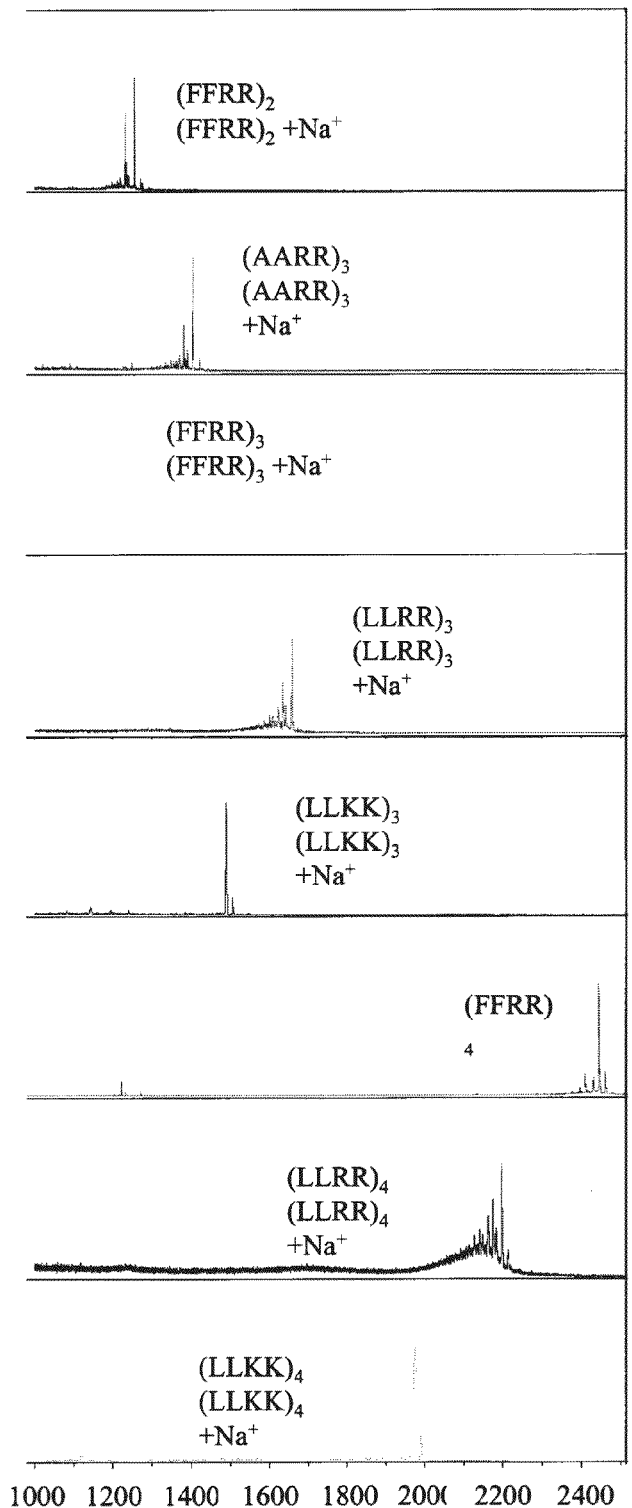
Figure 7:
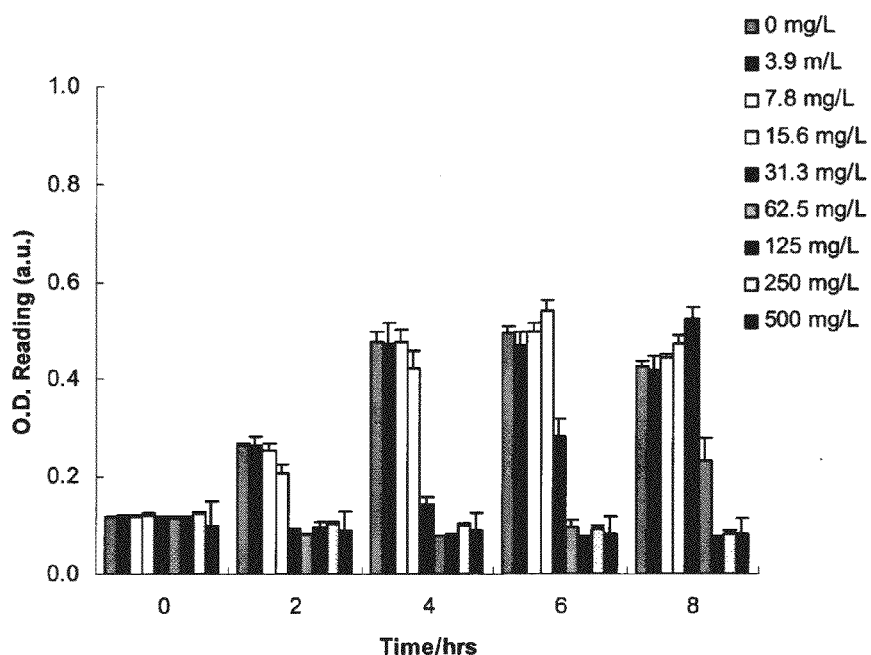
Figure 7:
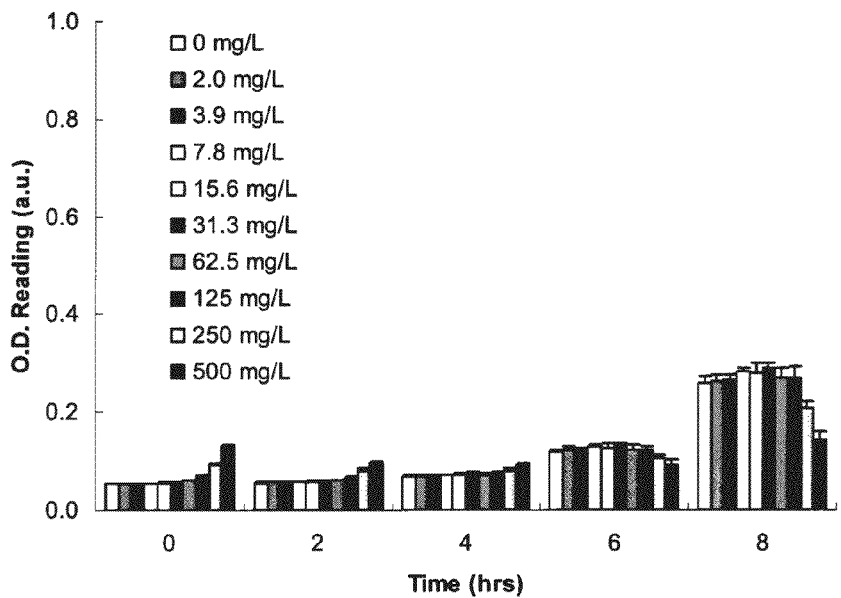
Figure 8:
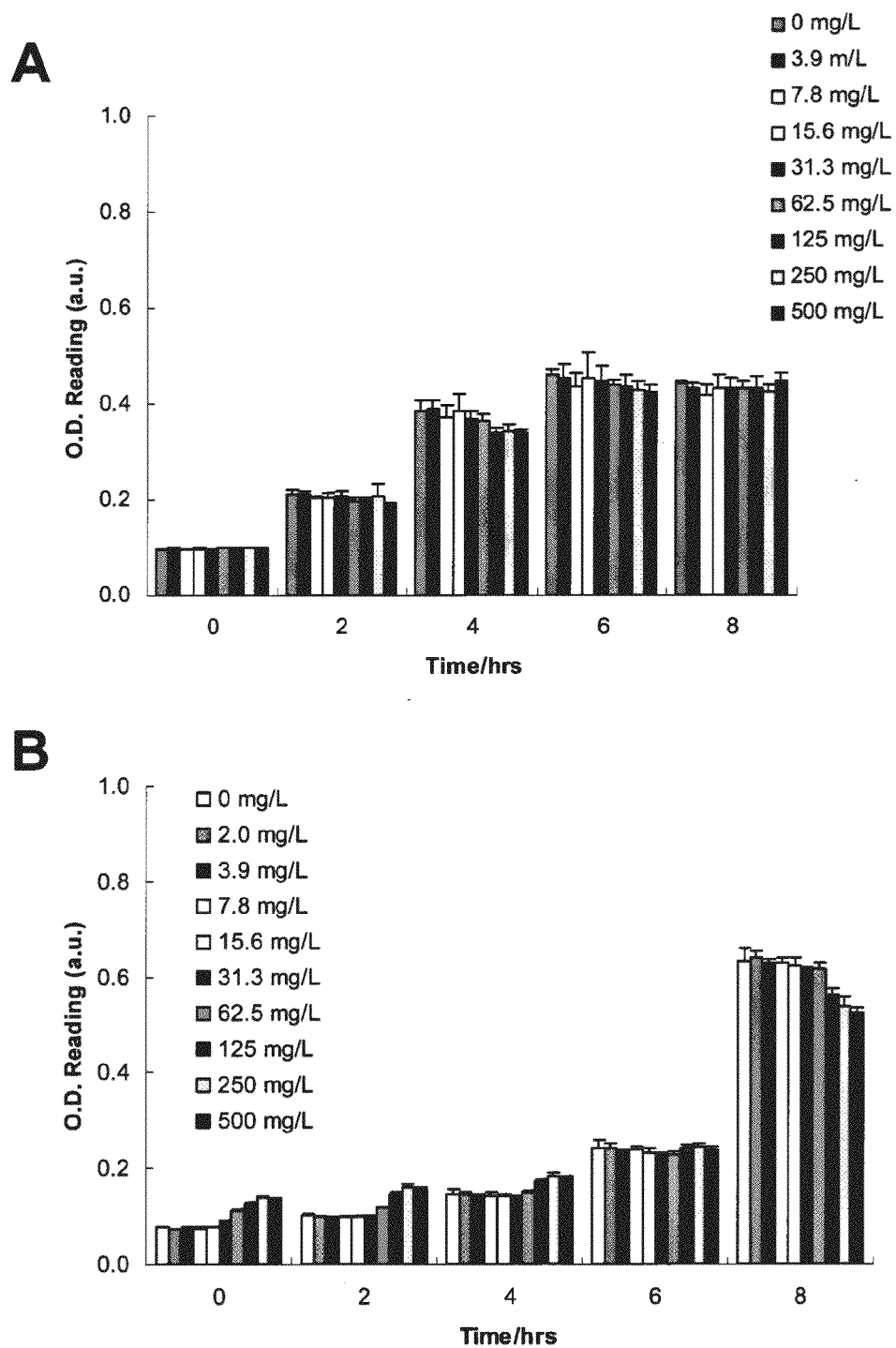
Figure 9:
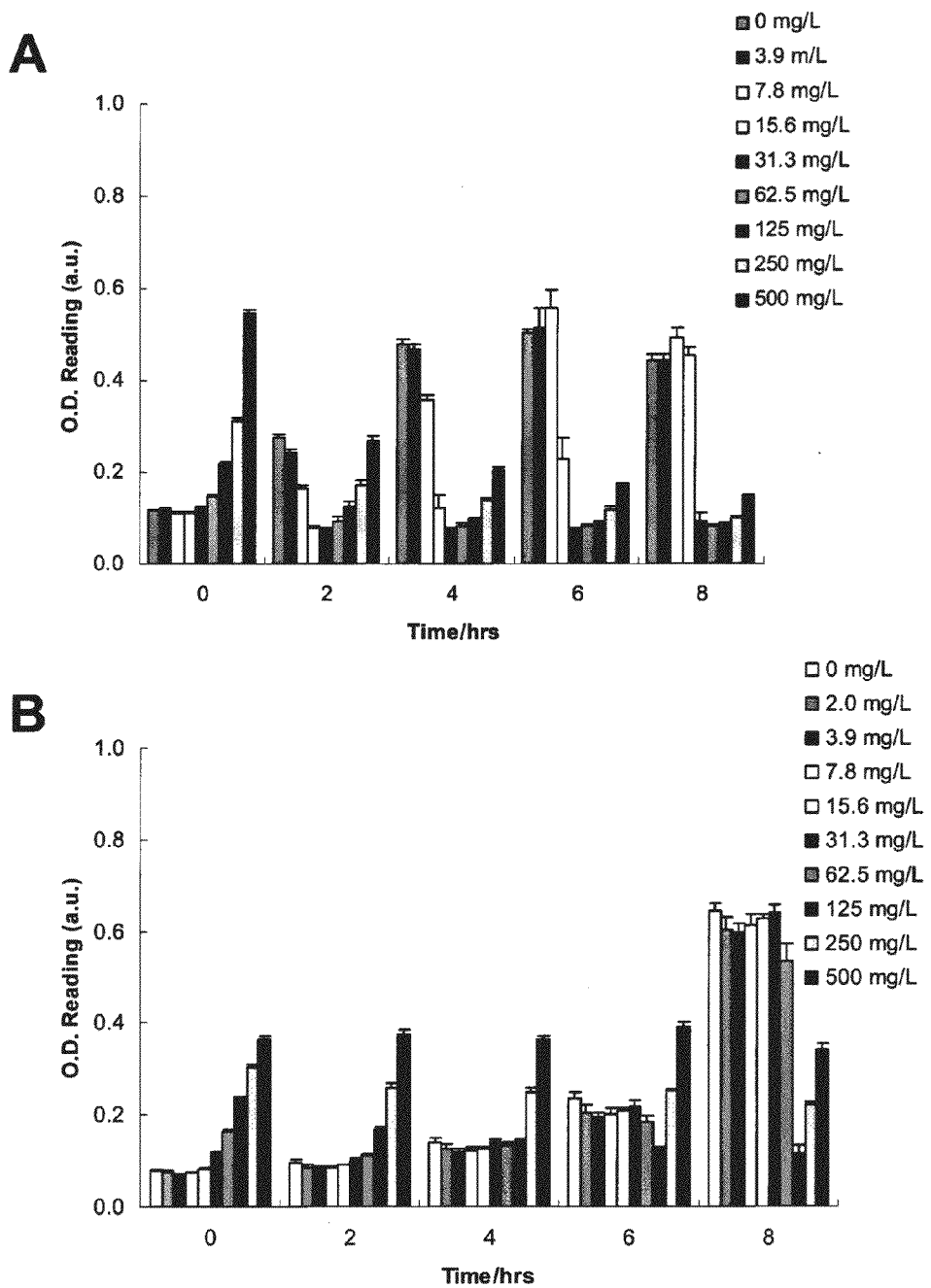
Figure 10:
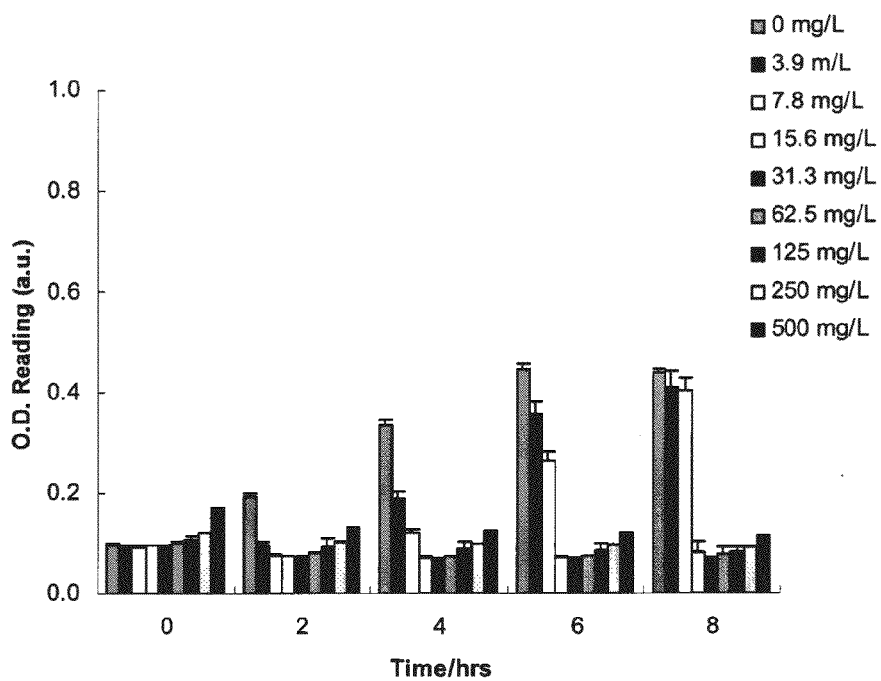
Figure 10:
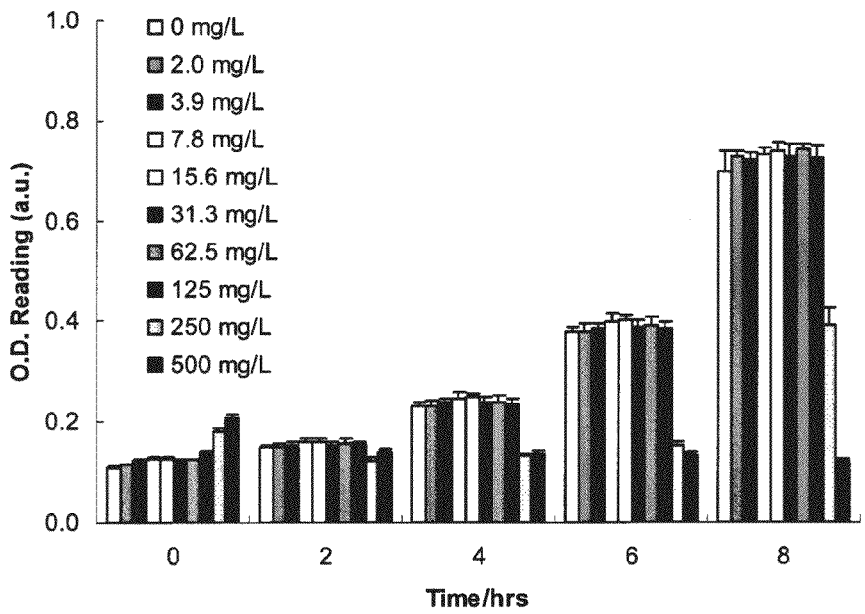
Figure 11:
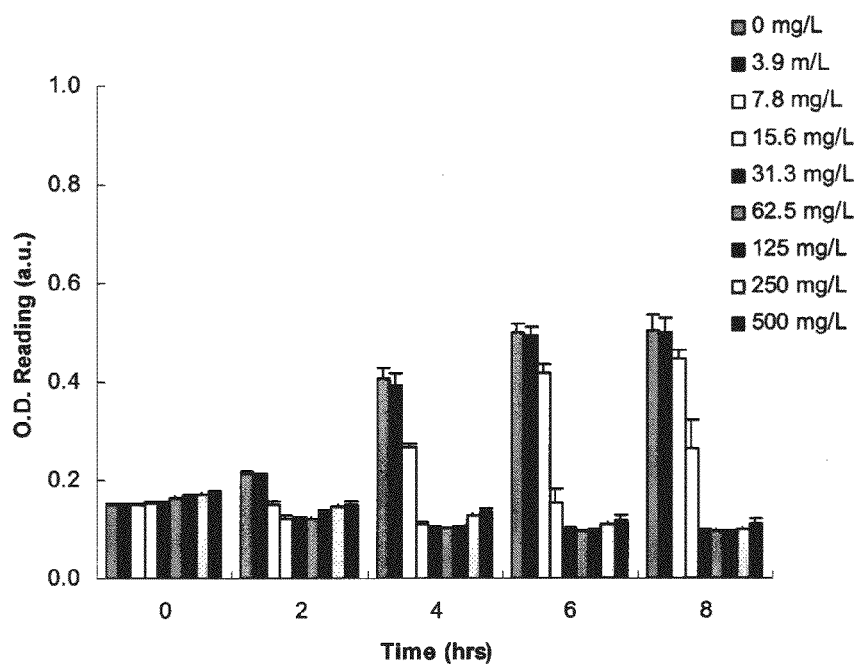
Figure 11:
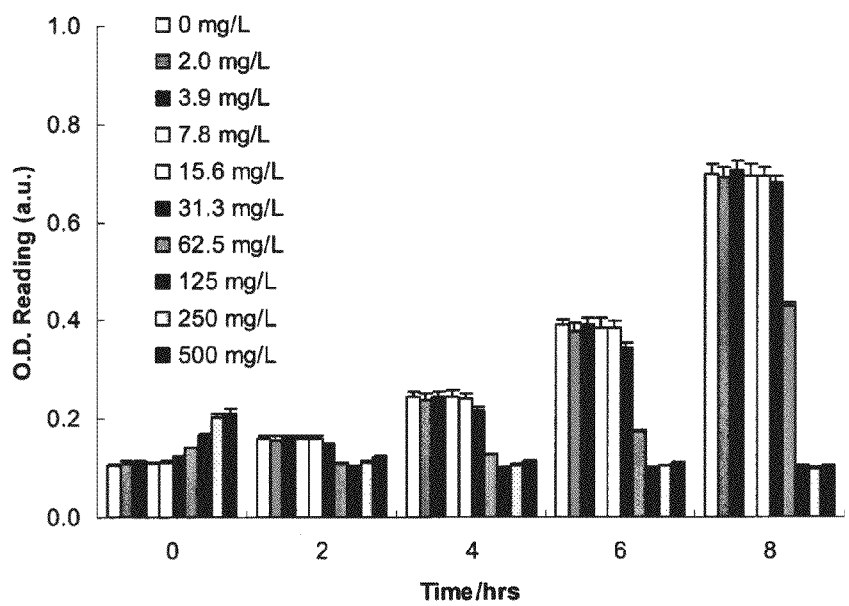
Figure 12:
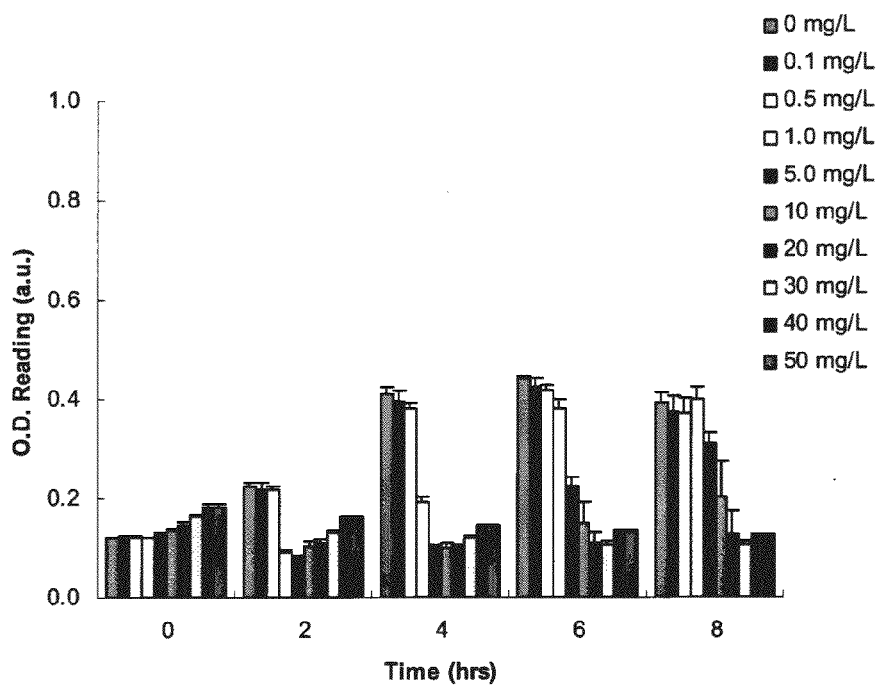
Figure 12:
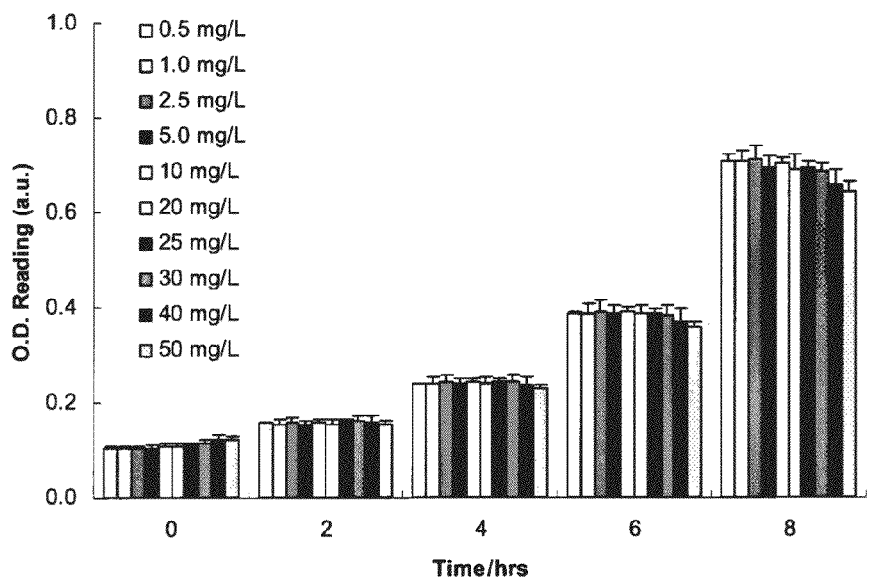
Figure 13:
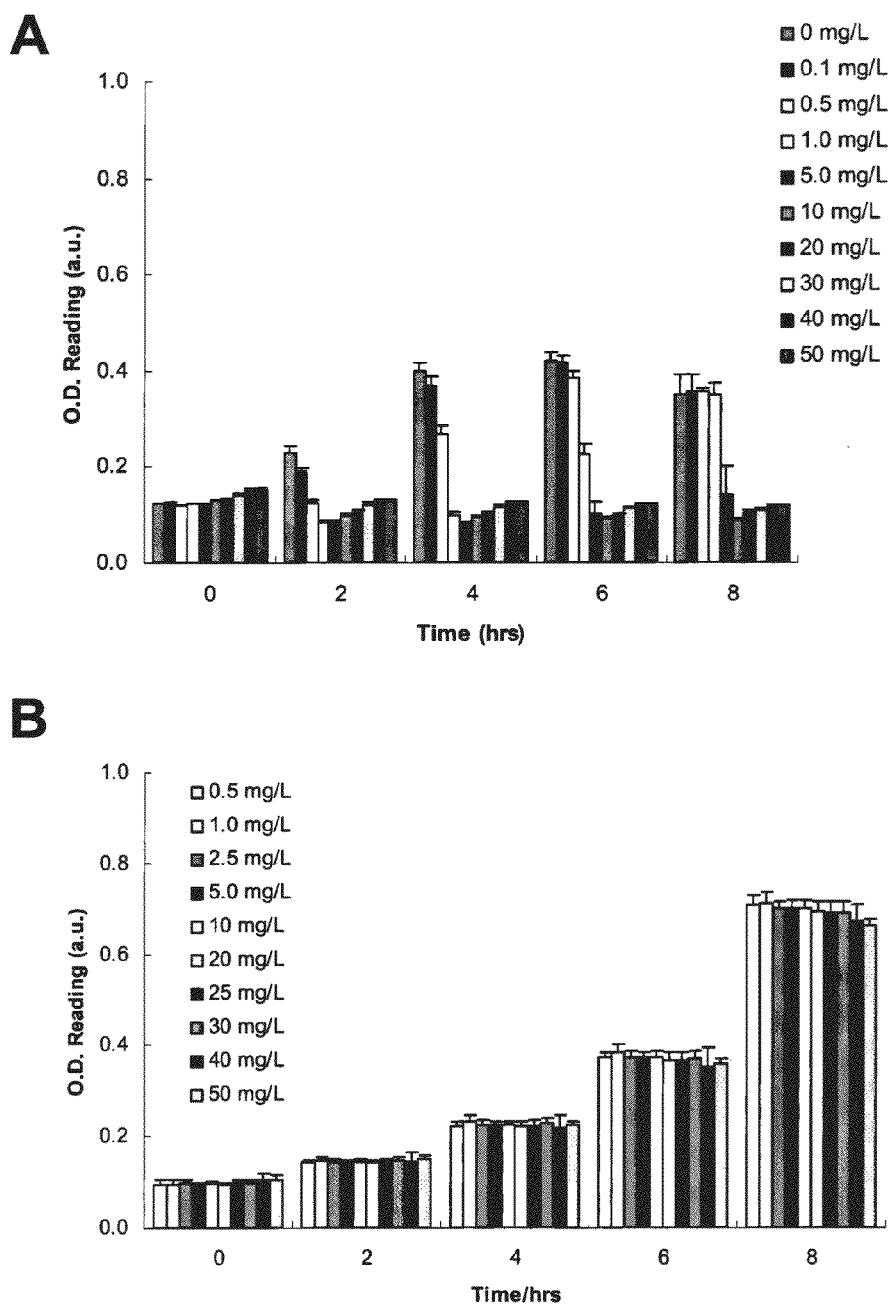
Figure 14:
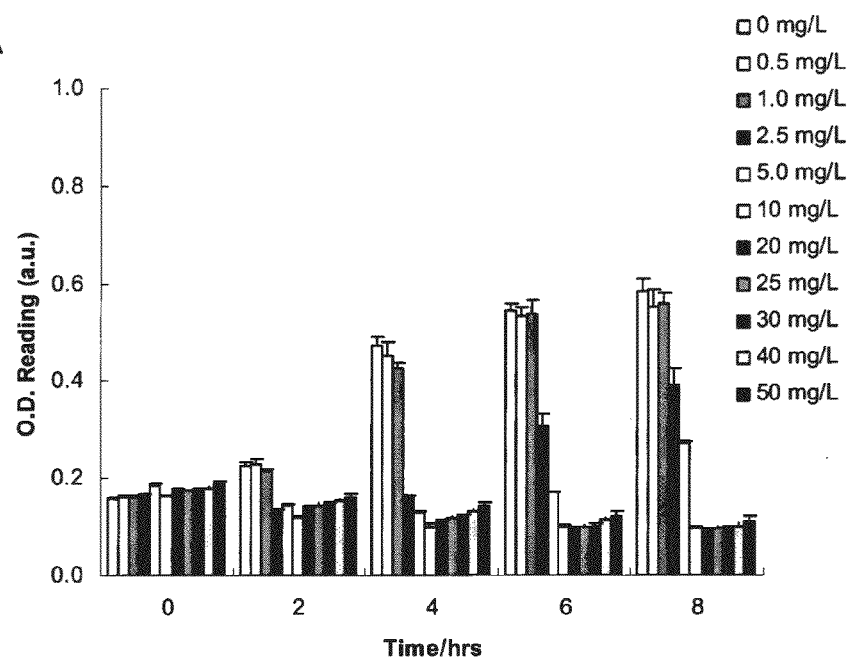
Figure 14:
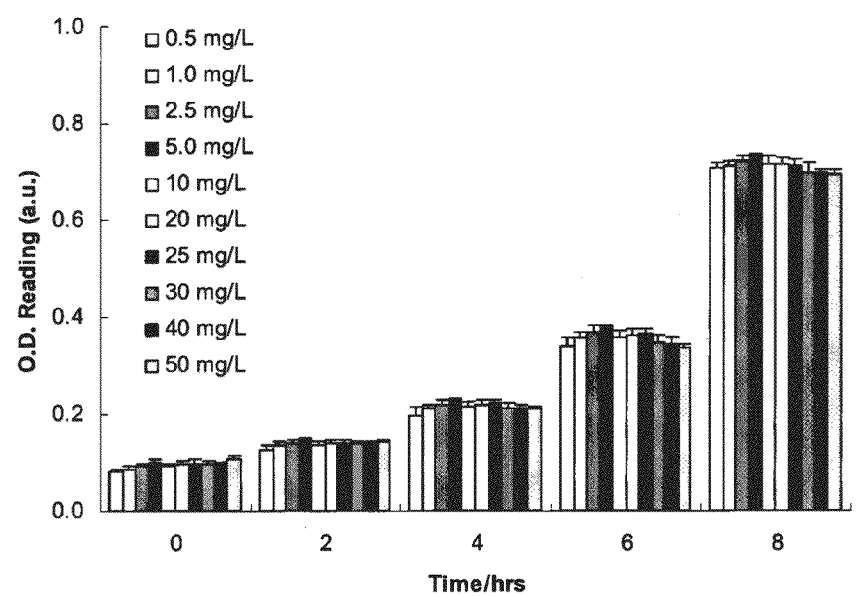
Figure 15:
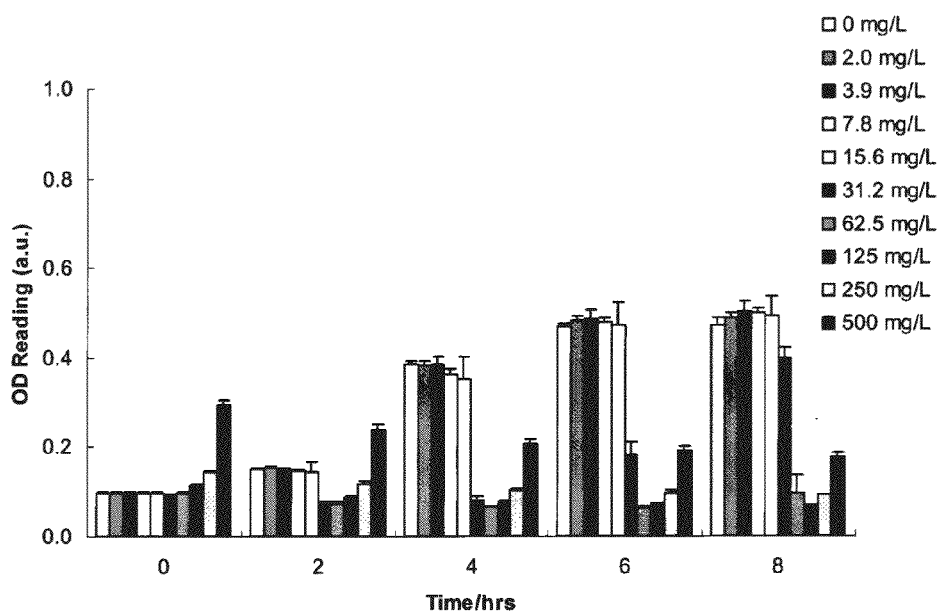
Figure 15:
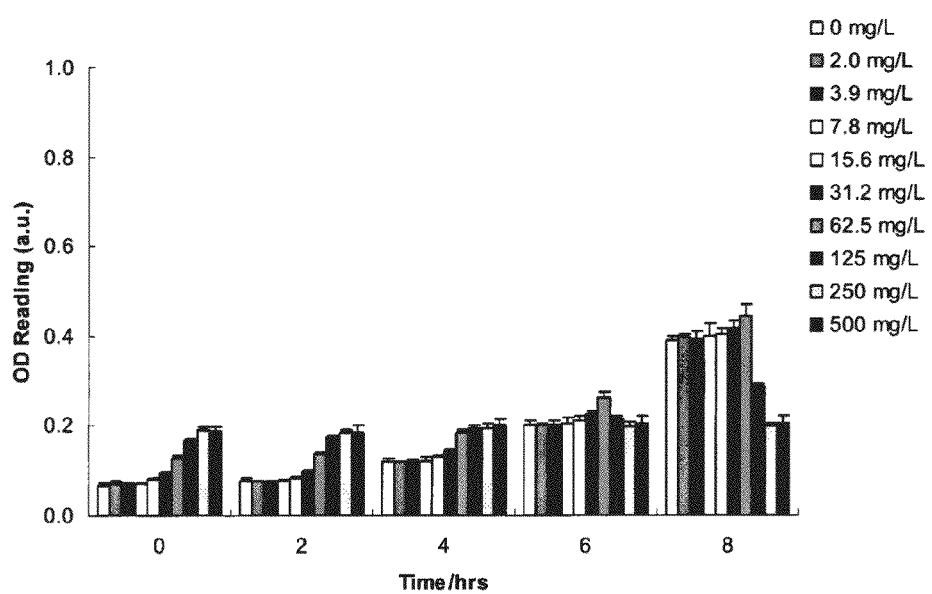
Figure 15:
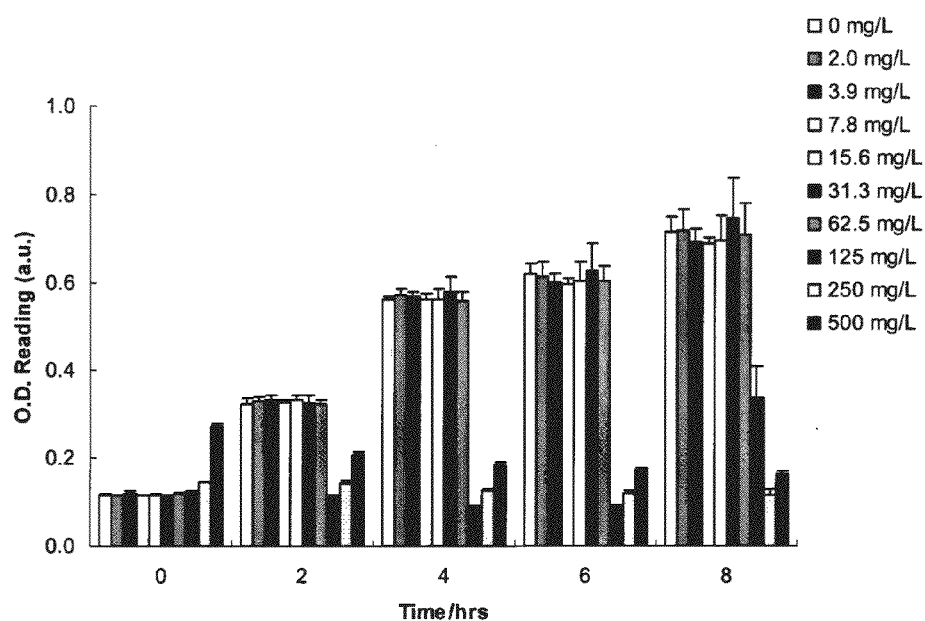
Figure 15:
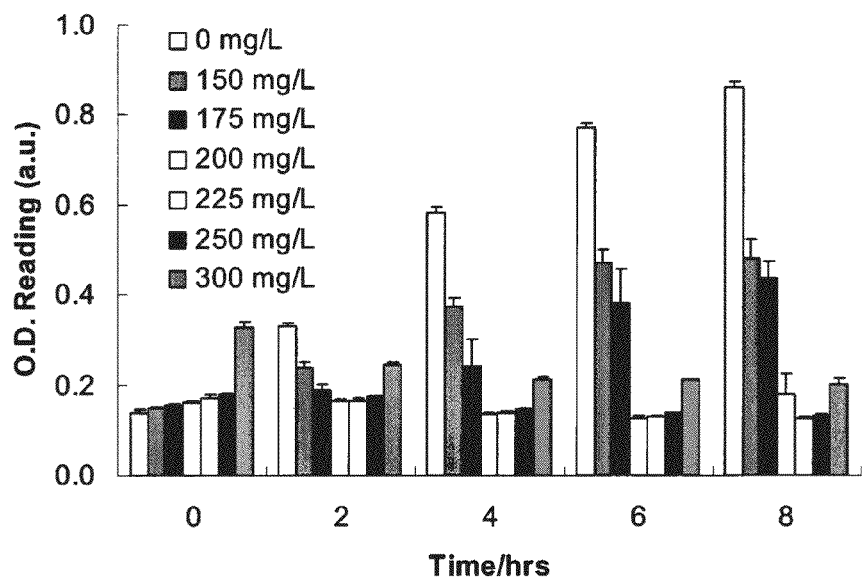
Figure 16:
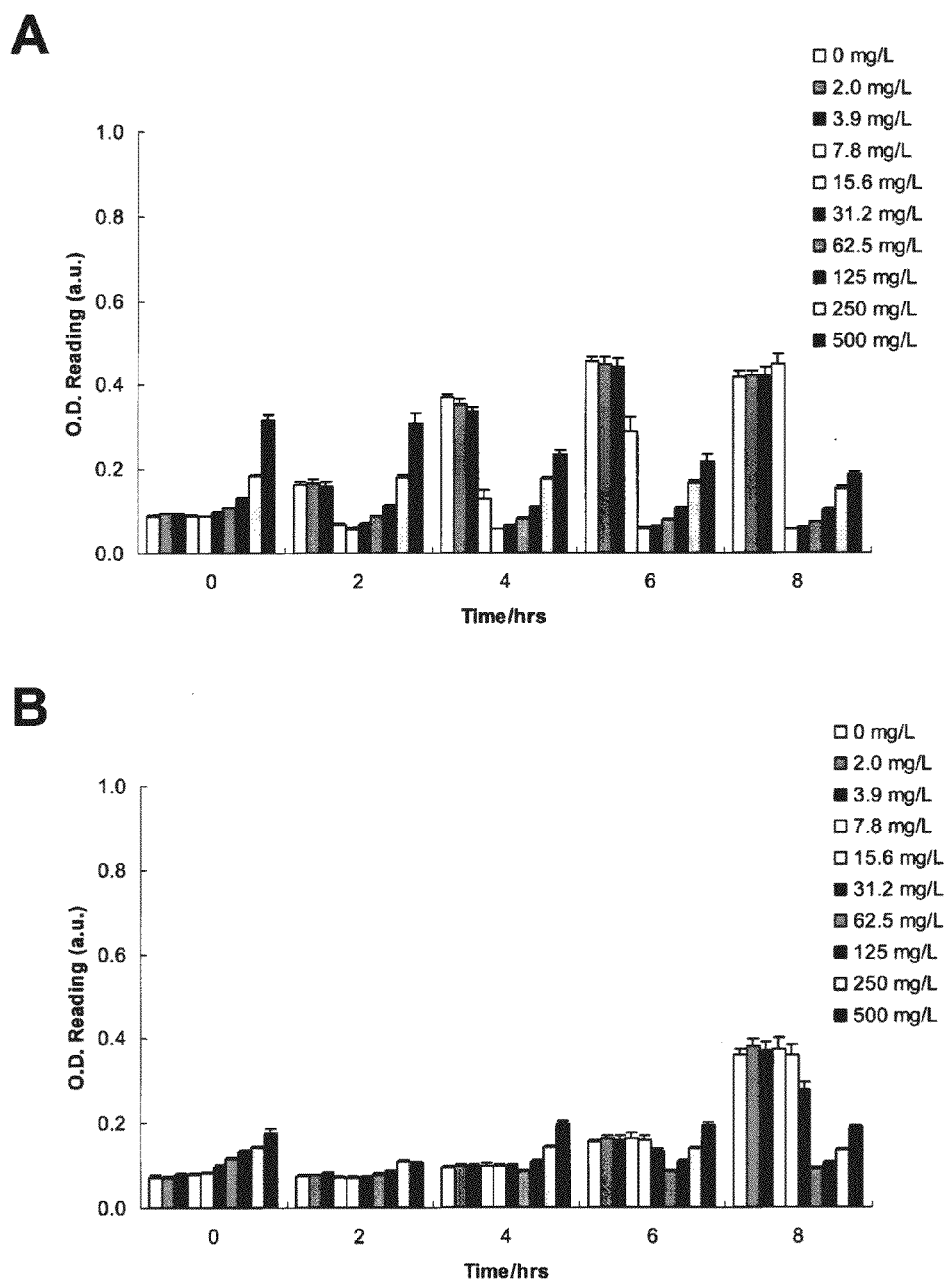
Figure 16:
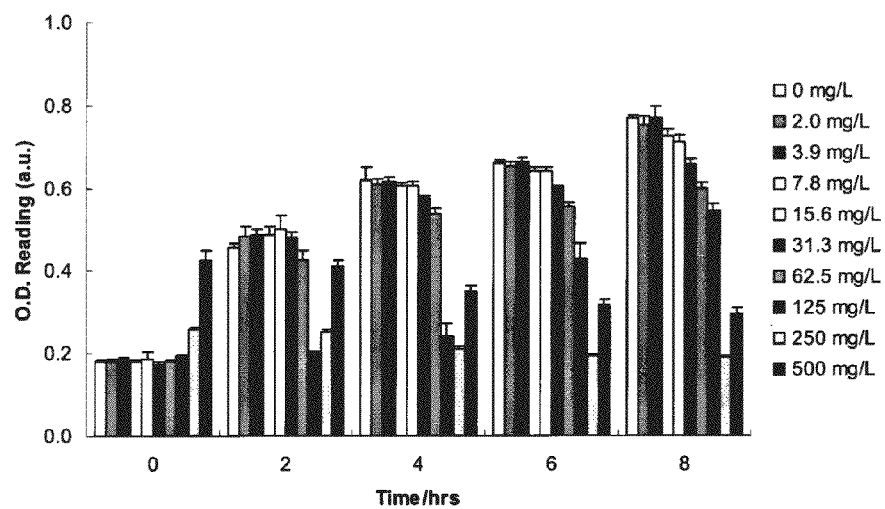
Figure 16:
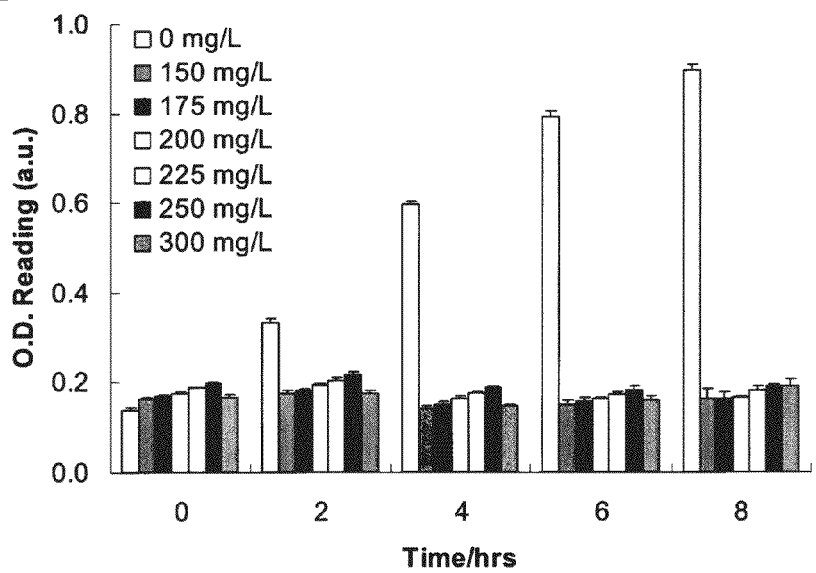
Figure 17:
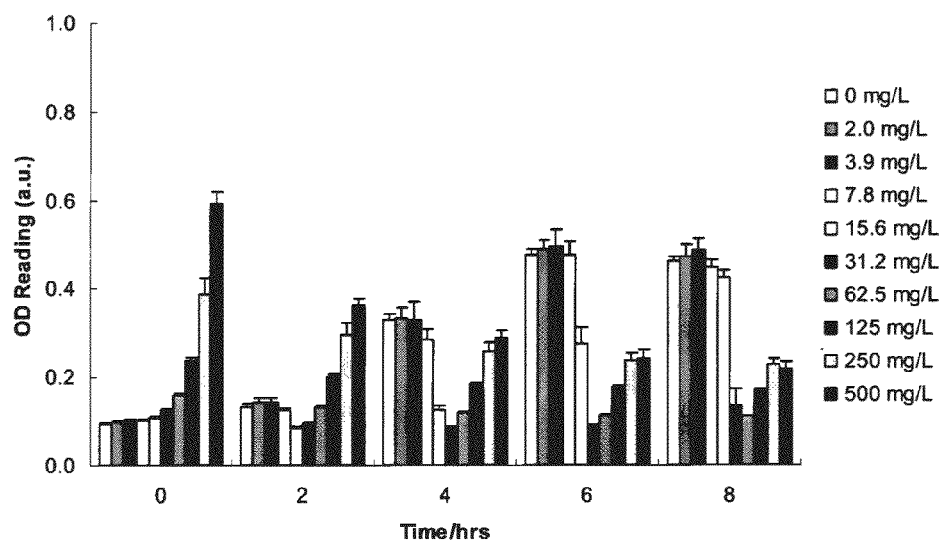
Figure 17:
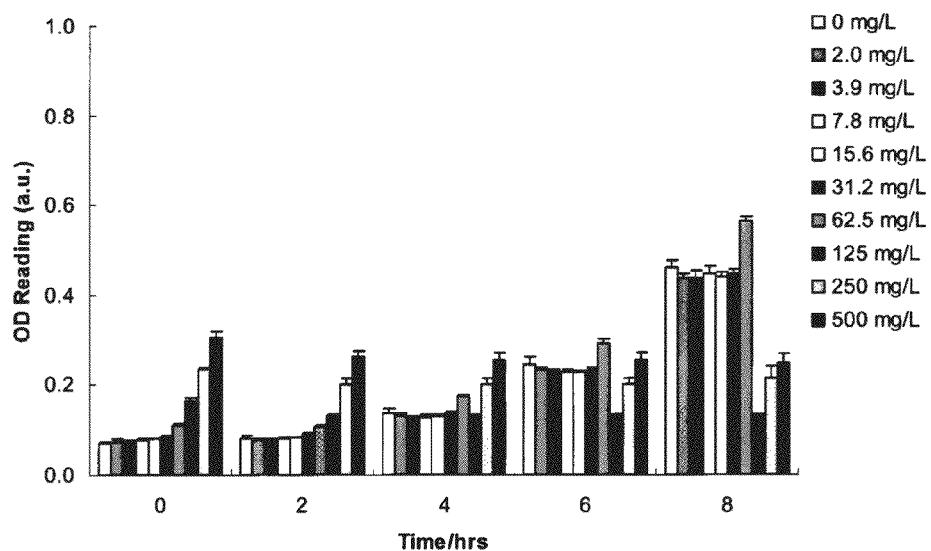
Figure 17:
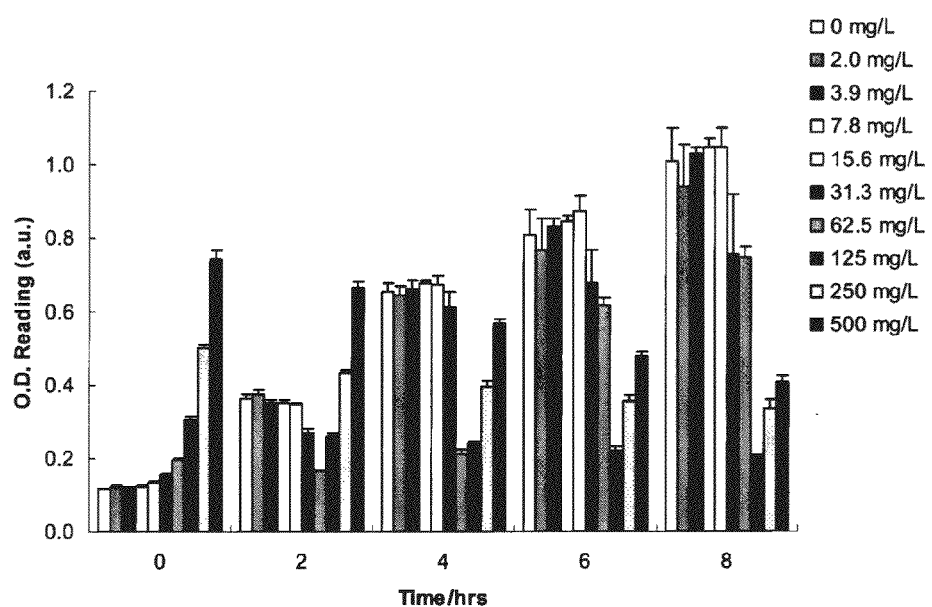
Figure 18:
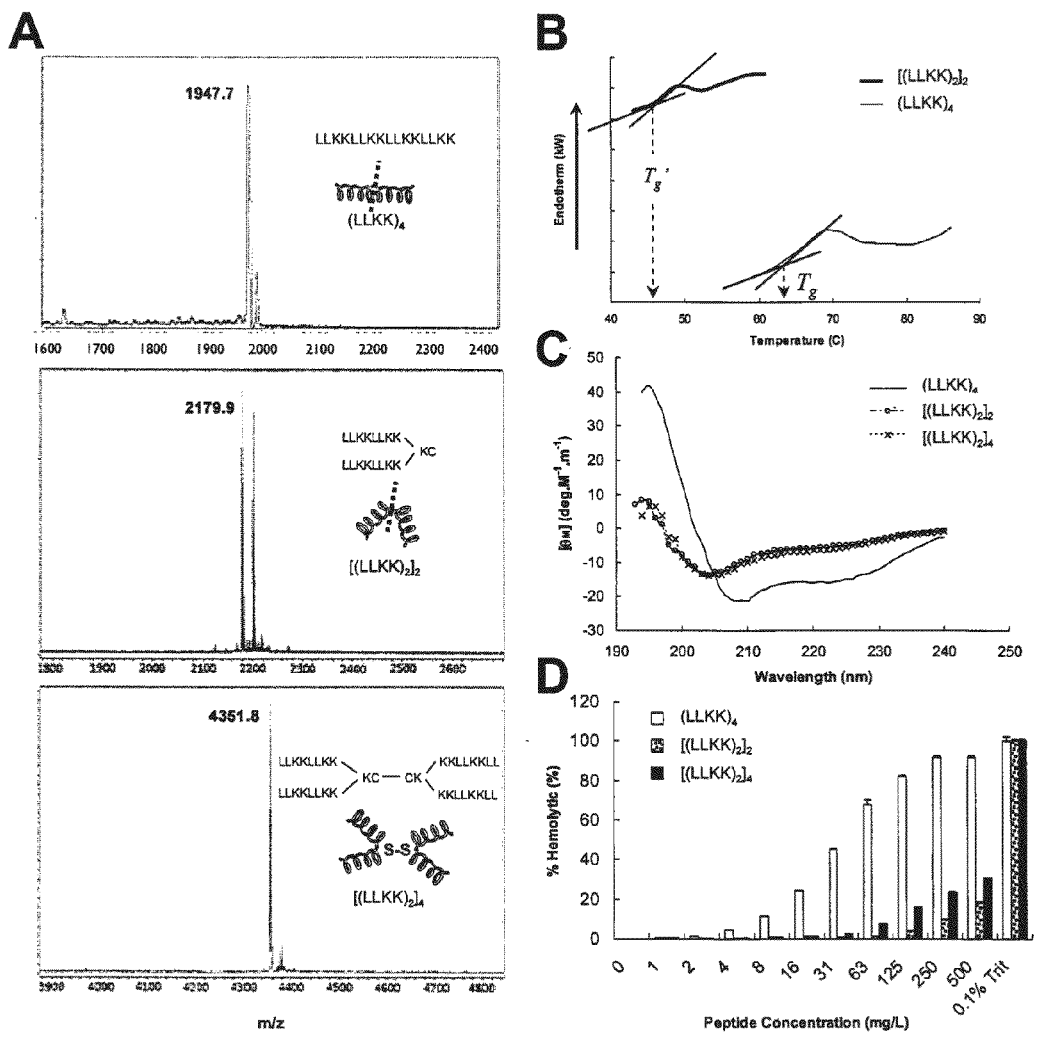
Figure 19:
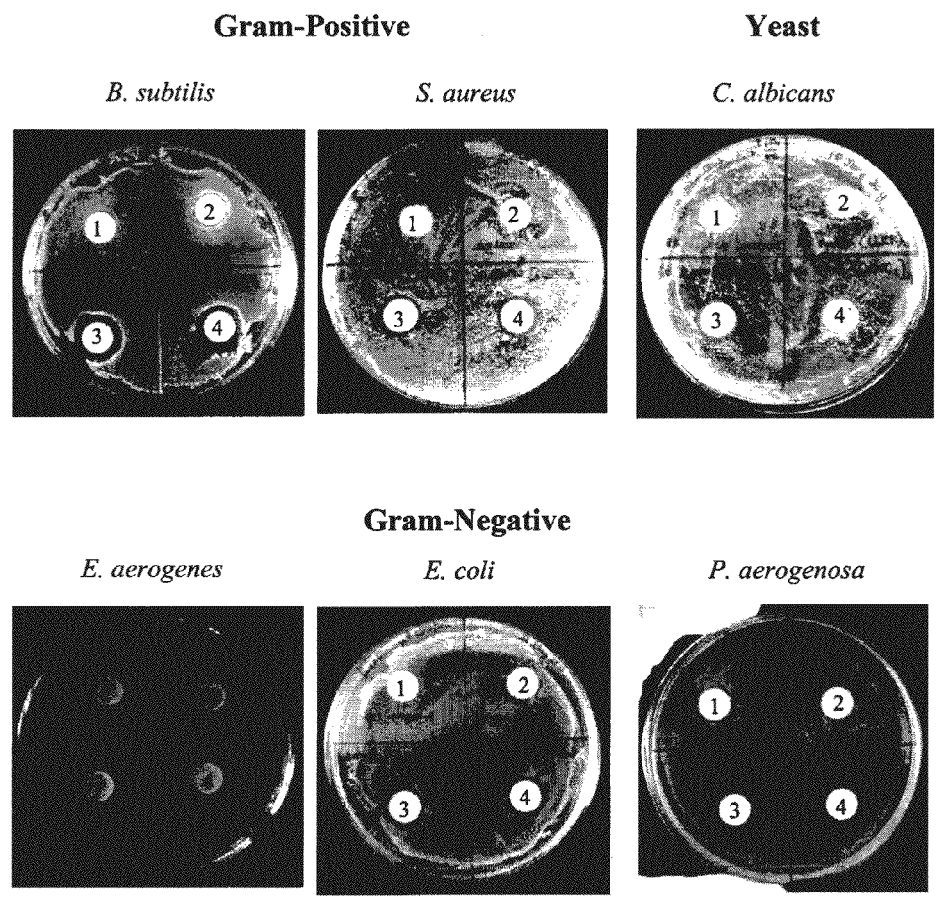
Figure 20:
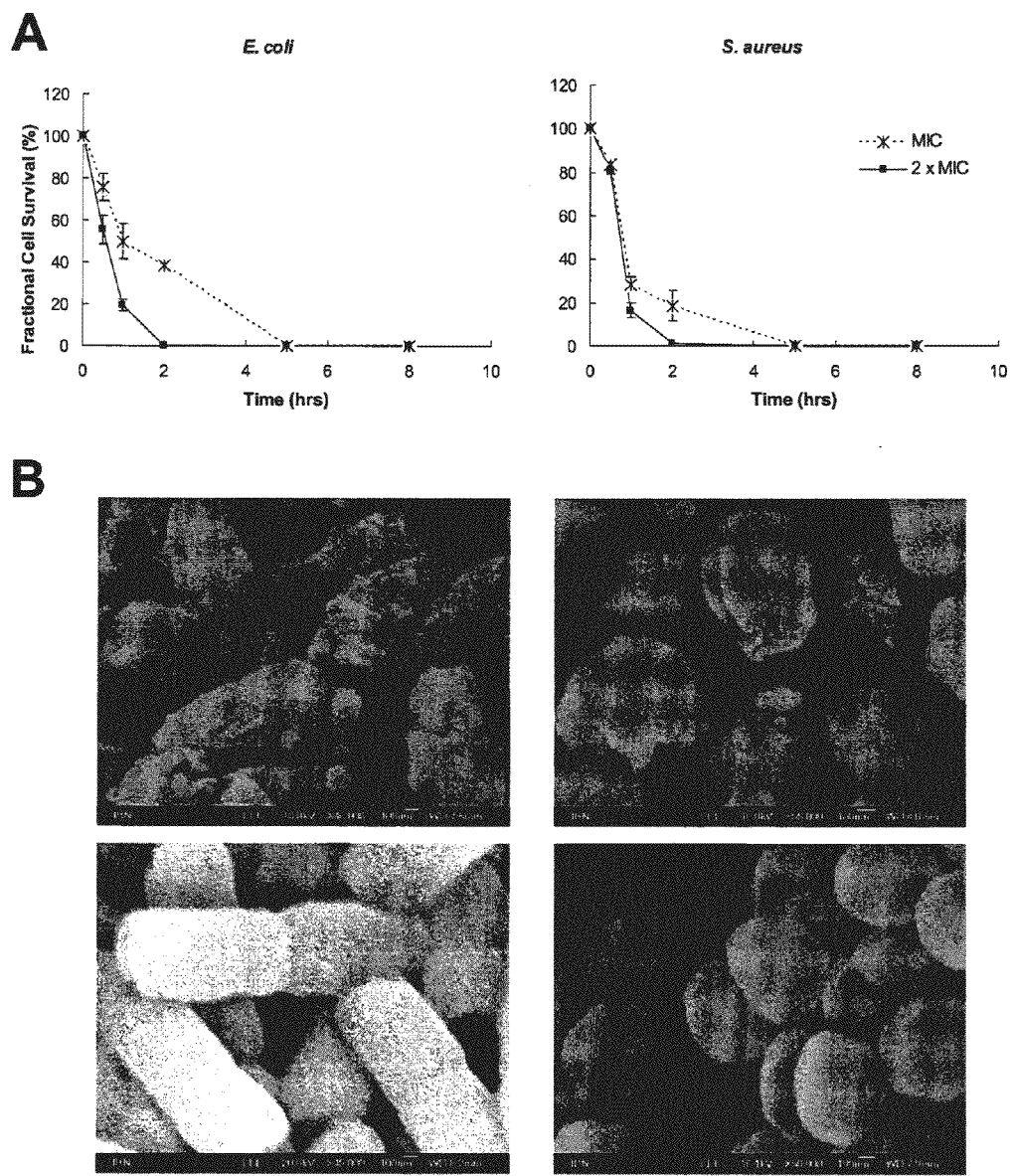
Figure 21:
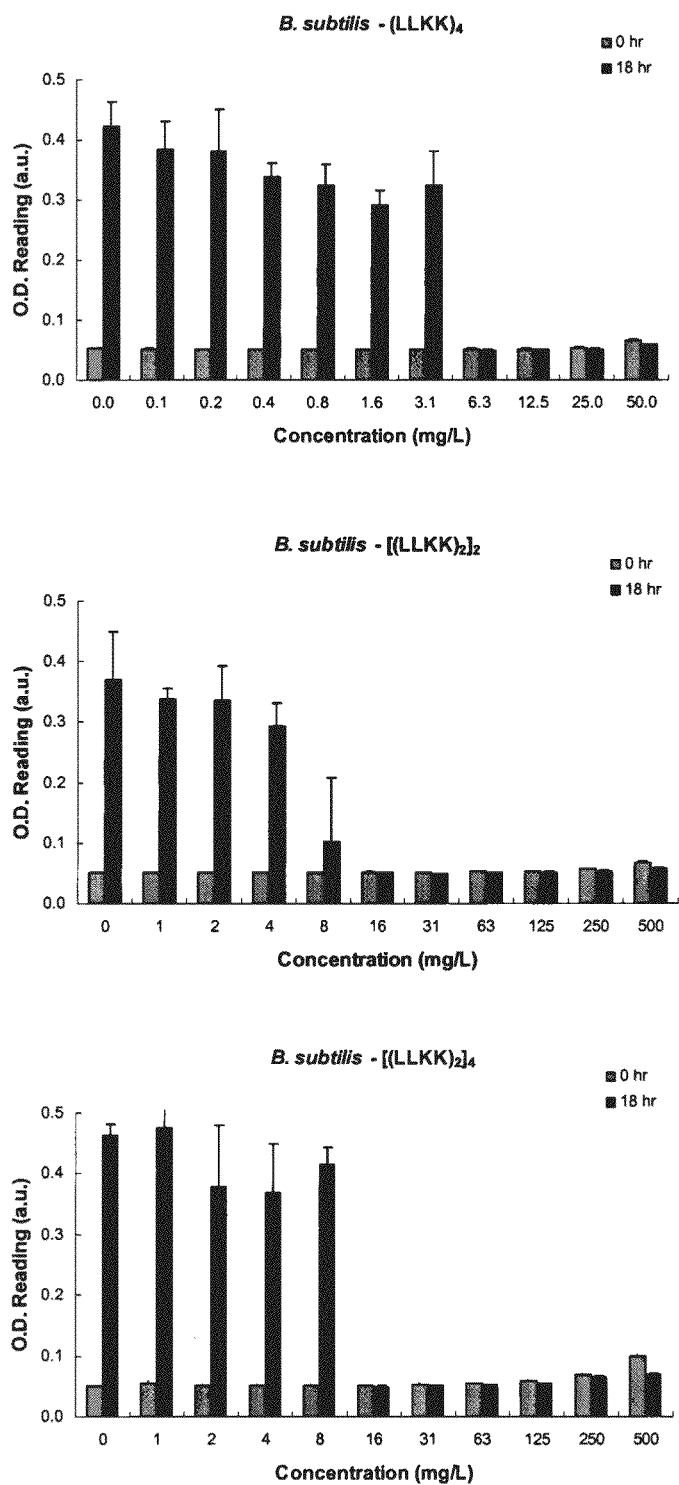
Figure 22:
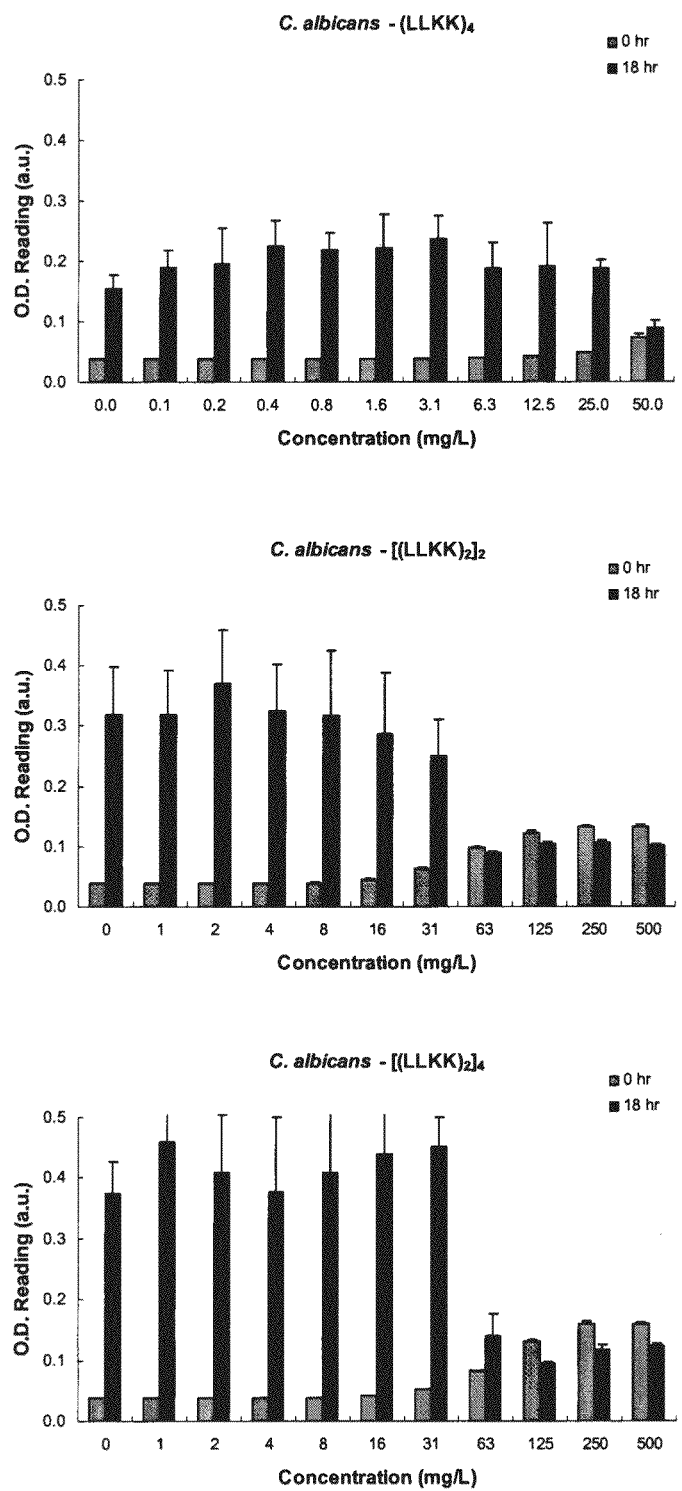
Figure 23:
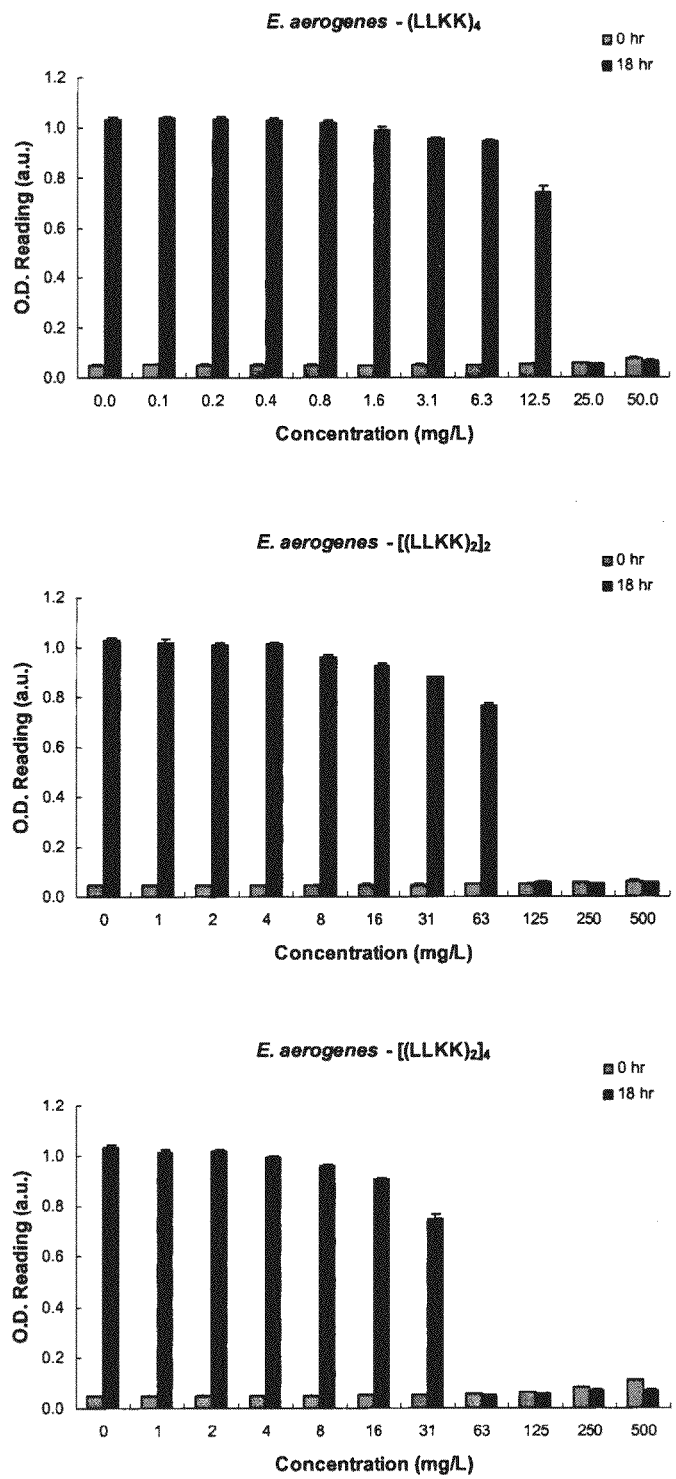
Figure 24:
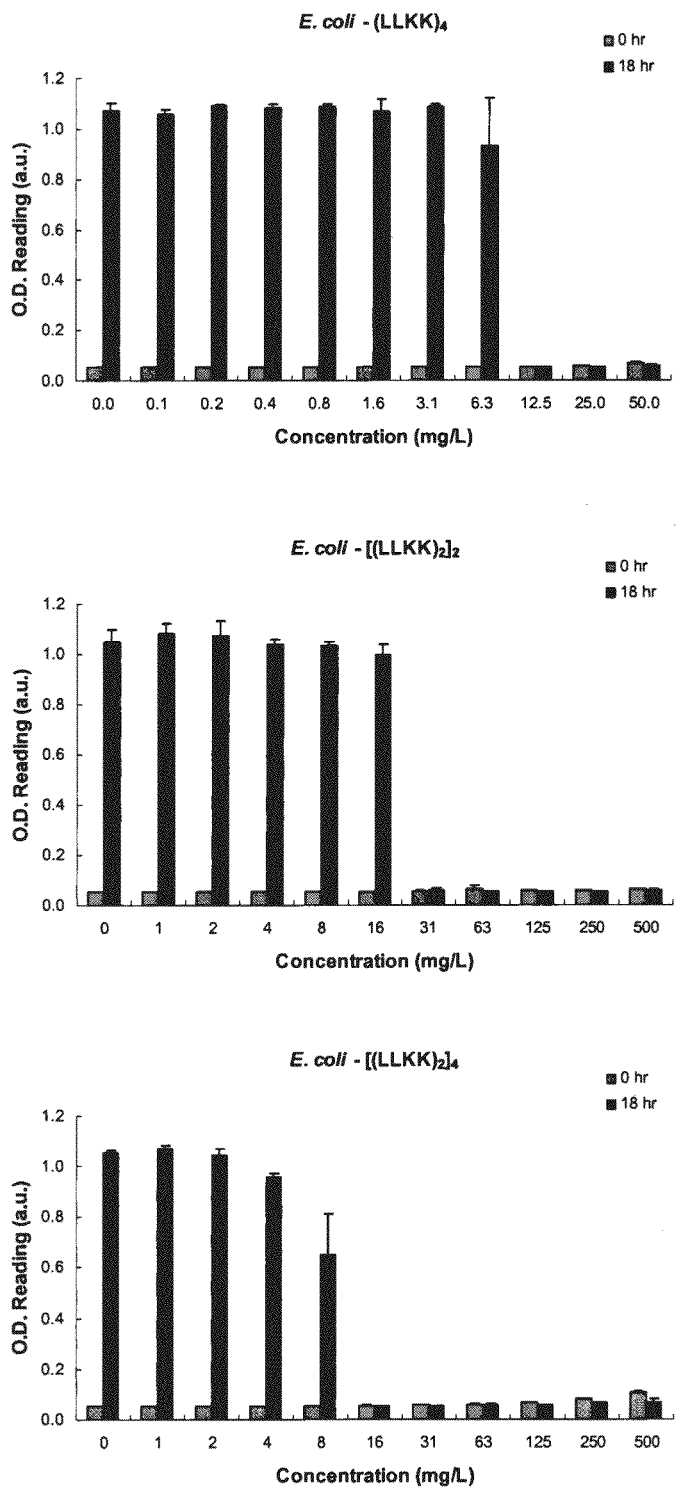
Figure 25:
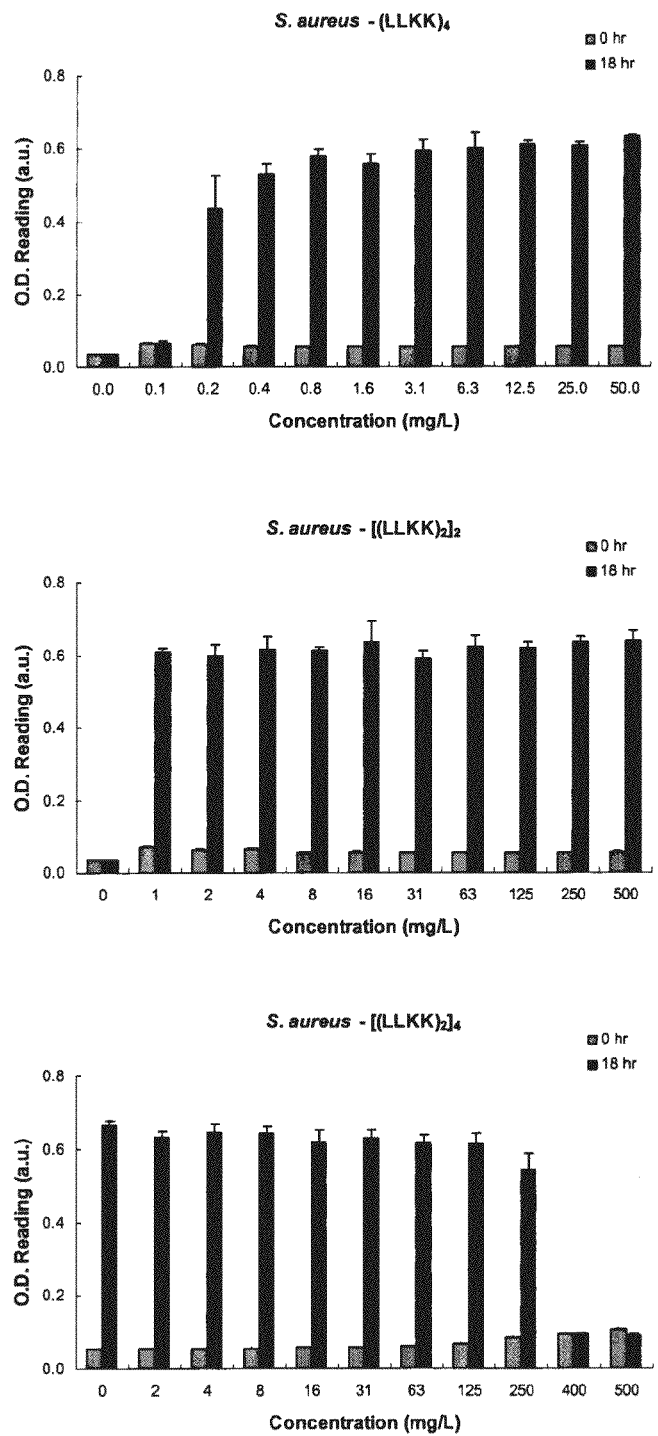
Figure 26:
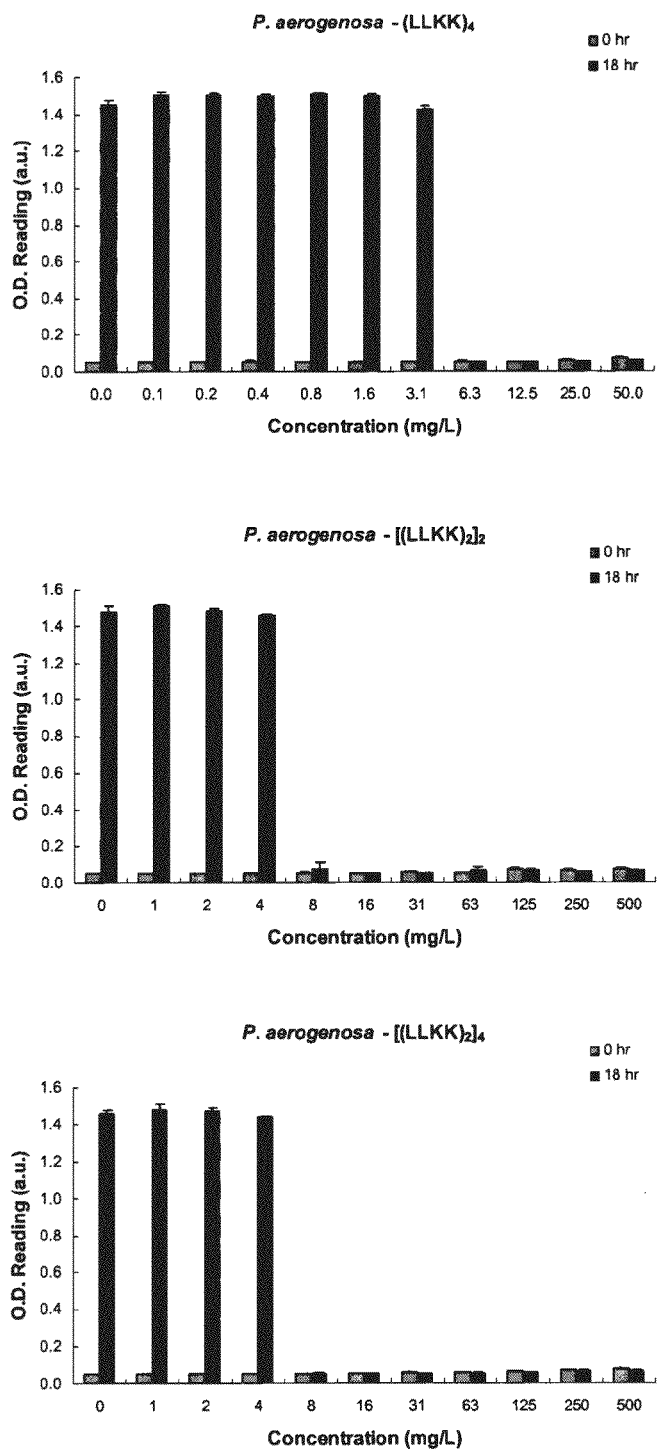
Figure 27:
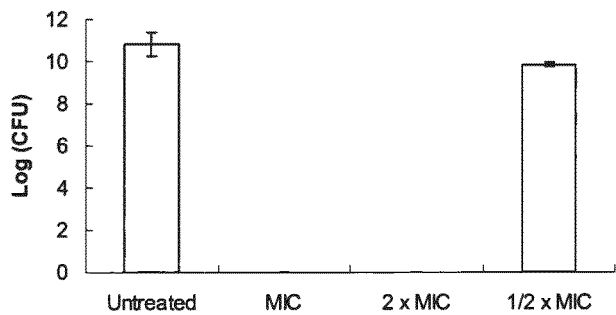
Figure 27:
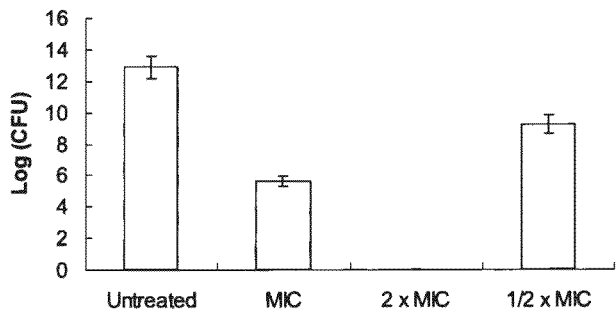

FIG. 3A shows SEM images of *B. subtilis* after incubation with the peptides of three repeat units at 50 mg/L (above MIC) for 2 hours; (AARR)$_3$ (SEQ ID NO: 3); (LLRR)$_3$ (SEQ ID NO 4); (FFRR)$_3$ (SEQ ID NO: 2); (LLKK)$_3$ (SEQ ID NO:5);

FIG. 3B shows SEM images of *E. coli* after treatment with peptides having sulfhydryl modifications, C(LLKK)$_2$C (SEQ ID NO: 10) and (LLKK)$_3$C (SEQ ID NO: 12), at 250 mg/L (above MIC) for 2 hours;

FIG. 4 shows SEM images of *B. subtilis* after incubation with (LLKK)$_3$ (SEQ ID NO: 5) peptide at 50 mg/L (above MIC) for various periods of time;

FIG. 5 shows secretion of (☐) IFN-α and (■) IFN-γ by human peripheral blood mononuclear cells stimulated by (LLKK)$_3$ (SEQ ID NO: 5) and LPS;

FIG. 6 shows MALDI-TOF MS spectra of α-helical antimicrobial peptides according to the present invention; SEQ ID NOs: 1, 3, 2, 4, 5, 6, 7 and 8 can be found from top to bottom, respectively;

FIG. 7 shows MIC measurements of (FFRR)$_2$ (SEQ ID NO: 1) against (A) *B. subtilis* and (B) *C. albicans*;

FIG. 8 shows MIC measurements of (AARR)$_3$ (SEQ ID NO: 3) against (A) *B. subtilis* and (B) *C. albicans*;

FIG. 9 shows MIC measurements of (FFRR)$_3$ (SEQ ID NO: 2) against (A) *B. subtilis* and (B) *C. albicans*;

FIG. 10 shows MIC measurements of (LLRR)$_3$ (SEQ ID NO: 4) against (A) *B. subtilis* and (B) *C. albicans*;

FIG. 11 shows MIC measurements of (LLKK)$_3$ (SEQ ID NO: 5) against (A) *B. subtilis* and (B) *C. albicans*;

FIG. 12 shows MIC measurements of (FFRR)$_4$ (SEQ ID NO: 6) against (A) *B. subtilis* and (B) *C. albicans*;

FIG. 13 shows MIC measurements of (LLRR)$_4$ (SEQ ID NO: 7) against (A) *B. subtilis* and (B) *C. albicans*;

FIG. 14 shows MIC measurements of (LLKK)$_4$ (SEQ ID NO: 8) against (A) *B. subtilis* and (B) *C. albicans*;

FIG. 15 shows MIC measurements of C(LLKK)$_2$C (SEQ ID NO: 10) against (A) *B. subtilis*, (B) *C. albicans*, and (C and D) *E. coli*;

FIG. 16 shows MIC measurements of (LLKK)$_3$C (SEQ ID NO: 12) against (A) *B. subtilis*, (B) *C. albicans*, and (C and D) *E. coli*;

FIG. 17 shows MIC measurements of C(LLKK)$_3$C (SEQ ID NO: 13) against (A) *B. subtilis*, (B) *C. albicans*, and (C) *E. coli*;

FIG. 18A shows a schematic diagram and mass spectra of linear (LLKK)$_4$ (SEQ ID NO: 8), 2-arm [(LLKK)$_2$]$_2$, and star-like [(LLKK)$_2$]$_4$ α-helical peptides (A);

FIG. 18B shows differential scanning calorimetry spectra of linear (LLKK)$_4$ (SEQ ID NO: 8) and 2-arm [(LLKK)$_2$]$_2$, illustrating flexibility/rigidity difference of the helical backbone between the 2 peptides (endothermic transitions are upwards on the y-axis);

FIG. 18C shows circular dichroism (CD) spectra of linear (LLKK)$_4$ (SEQ ID NO: 8), 2-arm [(LLKK)$_2$]$_2$, and star-like [(LLKK)$_2$]$_4$;

FIG. 18D shows an analysis of the hemolytic activity of 2-arm [(LLKK)$_2$]$_2$ and star-like [(LLKK)$_2$]$_4$ α-helical peptides in comparison to the linear (LLKK)$_4$ (SEQ ID NO: 8) peptide;

FIG. 19 shows a qualitative analysis of antimicrobial activity of the linear (LLKK)$_4$ (SEQ ID NO: 8), 2-arm [(LLKK)$_2$]$_2$, and star-like [(LLKK)$_2$]$_4$ α-helical peptides by the drug diffusion assay (DDA) method;

FIG. 20A shows fractional microbial survival of *E. coli* (left) and *S. aureus* (right) after 30 minutes, 1 hour, 2 hours, 5 hours, and 8 hours of treatment with star-like α-helical [(LLKK)$_2$]$_4$ peptide at MIC and 2×MIC;

FIG. 20B shows SEM images of *E. coli* (left) and *S. aureus* (right) treated with the star-like peptide for 1 hour (top) or untreated (bottom), wherein scale bars represent 100 nm;

FIGS. 21, 22, 23, 24, 25 and 26 show MIC determination for the linear (LLKK)$_4$ (SEQ ID NO: 8), 2-arm [(LLKK)$_2$]$_2$, and star-like [(LLKK)$_2$]$_4$ α-helical peptides against *B. subtilis, C. albicans, E. arogenes, E. coli, S. aureus* and *P. aeruginosa*, respectively; and FIG. 27 shows 18 hours end-point colony formation units (CFUs) of *E. coli* (left) and *S. aureus* (right) treated with growth medium (untreated) and star-like [(LLKK)$_2$]$_4$ peptide at MIC, 2×MIC, and ½×MIC concentrations.

EXAMPLES

The present invention is now further described by means of the following examples, which are meant to illustrate the present invention and not to limit it.

1. Linear Antimicrobial Peptides 1.1 Materials and Methods

Materials

Peptides were obtained from GL Biochem (Shanghai, China), and their fidelity was further confirmed via matrix-assisted laser desorption/ionization time-of-flight mass spectroscopy (MALDI-TOF MS, Model Autoflex II, Bruker Daltonics Inc., U.S.A.), using α-cyano-4-hydroxycinnamic acid as matrix. The purity of the peptides was also tested to be more than 95% with analytical reverse phase (RP)-HPLC. α-Cyano-4-hydroxycinnamic acid (HCCA) was purchased from Sigma-Aldrich (Singapore) and used in saturated acetonitrile/water (1:1 volume ratio) after being re-crystallized. Sodium dodecyl sulphate (SDS) micelle solution (10% w/v in DI water) was obtained from 1$^{st}$ Base (Malaysia) and used upon dilution to the desirable concentration range. Tryptic soy broth (TSB) powder and yeast mould broth (YMB) powder were purchased from BD Diagnostics (Singapore) and used to prepare the microbial broths according to the manufacturer's instructions. Phosphate-buffered saline solution at 10× concentration was purchased from 1st Base (Malaysia) and used after dilution to the desired concentration. Ethanol (analytical grade, 99%) and glutaraldehyde (synthetic grade, 50% in H$_2$O) were purchased from Sigma Aldrich (Singapore) and used as received. *B. subtilis* and *C. albicans* were obtained from ATCC (U.S.A.) and re-constituted according to the suggested protocols. Red blood cells used in the experiments were obtained from rats maintained at the Animal Handling Units of the Biomedical Research Centers (Singapore). Human peripheral blood mononuclear cells (PB-MCs) were extracted from healthy blood donors and maintained with RPMI medium supplemented with 10% lowendotoxin fetal bovine serum (FBS) and 1% penicillin-streptomycin. Granulocyte macrophage-colony stimulating factor (GM-CSF) and lipopolysaccharide were purchased from Sigma-Aldrich and used as received. Enzyme-linked immuno-sorbent assay (ELISA) kit for human interferons alpha (IFN-α, Cat No. 41100-1) and gamma (IFN-γ, Cat No. 41500-1) detection was purchased from PBL Interferon Source (VCell Science, Singapore), and used according to the suggested manufacturer's protocol.

Peptide Characterization

The peptides were synthesized by the standard Fmoc-solid phase peptide synthesis protocol at GL Biochem (Shanghai, P. R. China). The fidelity of the synthesis was confirmed via MALDI-TOF MS and RP-HPLC techniques. An equal volume of peptide aqueous solution (0.5 mg/mL) and α-cyano-4-hydroxycinnamic acid (HCCA) matrix solution (saturated in acetonitrile/water mixture at 1:1 volume ratio) were pre-mixed and spotted onto the MALDI ground-steel target plate to measure the molecular weight of the peptide. The same peptide solution was also run through a RPHPLC (with C-18 as the stationary phase, and the mixture of acetonitrile and water as the mobile phase with a gradient being varied from 5% to 20% acetonitrile from 0 to 20 minutes). From the area of the chromatograms obtained, the purity of the peptides was estimated to be more than 95%.

Circular Dichroism (CD) Spectroscopy

Peptide solutions were prepared to contain 0.5 mg/mL peptides dissolved in deionised (DI) water or 25 mM SDS surfactant. The CD spectra of the peptide solutions were recorded at room temperature with a CD spectropolarimeter (JASCO, J-810), using a quartz cell having 1.0 mm path length. The spectra were obtained from 190 to 240 nm with solvent subtracted at 10 nm/min scanning speed, and averaged from 3 runs of each sample. The acquired CD signal spectra were then converted to mean residue ellipticity by using the following equation:

$$\theta_M = \frac{\theta_{obs}}{10} \cdot \frac{M_{RW}}{c \cdot l}$$

where $\theta_M$ is residue ellipticity [deg. M$^{-1}$·m$^{-1}$], $\theta_{obs}$ is the observed ellipticity corrected for the buffer at a given wavelength [mdeg], $M_{RW}$ is residue molecular weight ($M_w$/number amino acids), c is peptide concentration [mg/mL], and l is the path length [cm].

Minimum Inhibitory Concentration (MIC) Measurements

Microbial cells were firstly re-constituted from its lyophilized form according to the manufacturer's protocol. Bacterial cells were cultured in tryptic soy broth (TSB) at 37° C., and yeast cells were cultured in yeast mould broth (YMB) at room temperature under constant shaking at 100 rpm. Broth containing an antimicrobial peptide was prepared at various concentrations (0.98, 1.95, 3.90, 7.81, 15.63, 31.25, 62.5, 125, 250, 500 mg/L) and transferred into a 96-well tissue culture plate (100 μL/well). Microorganism was first inoculated overnight to enter its log growth-phase. An equal volume of microorganism solution (100 μL) was added into each well of the 96-well plate containing the antimicrobial peptide. Prior to this mixing, the concentration of microorganism solution was adjusted to give an initial optical density (O.D.) reading of 0.1-0.2 at 600 nm wavelength. The growth of the microorganism was observed upon introducing the antimicrobial peptide by measuring the O.D. readings at 2 hour intervals for up to 8 hours. The MIC was taken as the concentration of the antimicrobial peptide at which no microbial growth was observed with unaided eye and microplate reader (TECAN, Switzerland) at the end of 8 hours incubation. Broth containing microbial cells was used as the negative control, and each test was carried out in 6 replicates. The standard deviations of the 6 readings were reported as the error bars.

Hemolytic Activity Test

Fresh red blood cells were washed with PBS for three times, and were subjected to 25 times dilution with PBS to reach a concentration of approximately 4% (in volume) of the blood cells. The red blood cell suspension (100 μL) was placed into a 96-well cell culture plate and mixed with 100 μL of the antimicrobial peptide solution in PBS at concentrations of 0.98, 1.95, 3.90, 7.81, 15.63, 31.25, 62.5, 125, 250, 500 mg/L. The mixture was then incubated at 37° C. for 1 hour to allow for the hemolysis process to take place. At the end of incubation time, the non-hemolysed red blood cells were separated by centrifugation at 13000 g for 5 minutes. Aliquots (100 μL) of the supernatant were transferred into a new 96-well plate, and the hemoglobin release was measured by checking the UV-absorbance of the samples at 576 nm using a microplate reader (TECAN, Switzerland). Two controls were provided in this assay: an untreated red blood cell suspension in PBS was used as the negative control, and a solution containing red blood cells lysed with 0.1% Triton-X was used as the positive control. Each assay was performed in 6 replicates, and the data were expressed as means and standard deviations of the 6 replicates. Percentage of hemolysis was calculated using the following formula:

Hemolysis (%)=[(O.D.$_{576\,nm}$ of the treated sample−O.D.$_{576\,nm}$ of the negative control)/(O.D.$_{576\,nm}$ of positive control−O.D.$_{576\,nm}$ of negative control)]×100%.

Field Emission-Scanning Electron Microscopy (FE-SEM) Analysis of Bacterial Cells Bacterial cells were cultured in tryptic soy broth at 37° C. under constant shaking at 100 rpm. Similar treatments as the broth microdilution method were performed for a shorter period of incubation to prepare the treated bacterial sample. Briefly, broth containing an antimicrobial peptide (100 μL) was prepared at 50 mg/L (a concentration above the MIC of the peptide) and pipetted into a 96-well cell culture plate. Microorganism was first inoculated to enter its log growth-phase. An equal volume of microorganism solution (100 μL) was added into each well of the 96-well plate containing the antimicrobial peptide. The concentration of microorganism solution was adjusted to give an initial optical density (O.D.) reading of 0.1-0.2 at 600 nm wavelength. Peptide treatment of the bacterial cells was at 37° C. for 2 hours with 8 replicates, after which all the replicates were mixed into a microfuge tube and pelleted down at 5000 g for 5 minutes. For kinetic study of the antimicrobial actions, the incubation time with the antimicrobial agent was varied from 10, 20, 30, 40, 60, to 120 minutes. Following the incubation, bacterial cells were then washed with PBS for three times and fixed with 2.5% glutaraldehyde for 15 minutes, followed by washing with PBS twice. A final wash was performed with DI water, before the bacterial cells were pelleted down and dehydrated with a series of graded ethanol solution (30%, 50%, 70%, 95%, and 100%). Upon dehydration, the cells were then dried using a critical point dryer. Dried bacterial cells were then mounted on carbon tape, sputtered with platinum coating, and imaged under a field emission scanning electron microscope (JEOL JSM-7400F, Japan).

In Vitro Immunogenicity Test

Human peripheral blood mononuclear cells (PBMCs) were used to test on the effect of the peptides to induce non-specific immune response by monitoring the secretion of IFN-α and IFN-γ, two major cytokines produced by the innate immune system in its response to fight against infections/intrusions of foreign materials. These two cytokines were selected out of many cytokines as IFN-α has been widely accepted as the specific marker for bacterial and/or viral infections, whereas IFN-γ is known to be a more general marker resulting from immune responses towards foreign materials.

The human PBMCs used for this immune stimulation assay were extracted from freshly donated whole blood (from healthy donors from the National University Hospital, Singapore), via a standard Ficoll-Hypaque density centrifugation technique. Upon extraction from the human blood, PBMCs were re-constituted and maintained in RPMI growth medium (supplemented with 10% FBS and 1% penicillin-streptomycin) at 37° C. in the presence of 5% $CO_2$. To test the stimulation of IFN-α secretion by the human PBMCs after the peptide treatment, PBMCs were seeded at 3×10$^5$ cells/well in a 96-well plate (100 μL/well), and the cells were maintained with RPMI supplemented with granulocyte macrophage-colony stimulating factor (GM-CSF) (100 ng/mL) for 48 hours prior to treatment. Priming of monocytes with GM-CSF is known to be an absolute requirement for IFN-α secretion stimulated by many immunogenic materials such as lipopolysaccharide. Upon 48 hours of priming, PBMCs were treated with the designed antimicrobial peptide for 12 hours (100 μL at concentration of 250 mg/L), after which the growth medium was taken for ELISA test to detect the presence of any IFN-γ protein in the growth medium. Similarly, in order to test on the possibility of the antimicrobial peptide to stimulate IFN-γ secretion, which may result in an undesirable non-specific immunogenic response in vivo, PBMCs were seeded at 3×10$^5$ cells/well in a 96-well plate (100 μL/well). Unlike the immune response test for IFN-α, there is no requirement for PBMCs priming for IFN-γ stimulation. The seeded PBMCs were then treated with the antimicrobial peptide for 2 days (100 μL at concentration of 250 mg/L), after which the growth medium was taken for ELISA test to detect the presence of any IFN-γ protein in the growth medium. These tests were performed in triplicates, and were repeated with a blood sample from a different donor (National University Hospital, Singapore), to ensure the reproducibility from different blood samples. In these experiments, two controls were used: treatment with growth medium only (as negative control), and treatment with lipopolysaccharide (100 ng/μL) (as positive control).

1.2 Results

Peptide Characterization

The structure and molecular weight of the peptides were verified by MALDI-TOF MS. Table 1 summarizes the theoretically calculated molecular weight of the peptides and their measured molecular weights via MALDI-TOF MS (FIG. 6). It can be seen that each peptide has a measured molecular weight value that is in a very close agreement with its theoretical value. This suggests that the peptides were successfully synthesized.

TABLE 1

Peptides based on a α-helix strategy and their molecular weights

| Number of Repeat Units (n) | Repeat Units | Peptide Sequence | Theoretical Mw | Measured Mw* |
|---|---|---|---|---|
| 2 | FFRR (SEQ ID NO: 15) | FFRRFFRR-NH$_2$ (SEQ ID NO: 1) | 1230.49 | 1231.37 |
| 3 | FFRR (SEQ ID NO: 15) | FFRRFFRRFFRR-NH$_2$ (SEQ ID NO: 2) | 1837.22 | 1839.55 |
|  | AARR | AARRAARRAARR-NH$_2$ | 1380.63 | 1381.99 |

TABLE 1-continued

| | | | Theoretical Mw | Measured Mw* |
|---|---|---|---|---|
| | LLRR (SEQ ID NO: 16) | LLRRLLRRLLRR-NH$_2$ (SEQ ID NO: 3) | 1633.11 | 1634.74 |
| | LLKK (SEQ ID NO: 17) | LLKKLLKKLLKK-NH$_2$ (SEQ ID NO: 4) | 1465.03 | 1467.53 |
| 4 | FFRR (SEQ ID NO: 18) | FFRRFFRRFFRRFFRR-NH$_2$ (SEQ ID NO: 5) | 2443.94 | 2443.60 |
| | LLRR (SEQ ID NO: 15) | LLRRLLRRLLRRLLRR-NH$_2$ (SEQ ID NO: 6) | 2171.81 | 2174.35 |
| | LLKK (SEQ ID NO: 17) | LLKKLLKKLLKKLLKK-NH$_2$ (SEQ ID NO: 7) | 1947.70 | 1951.07 |
| | (SEQ ID NO: 18) | (SEQ ID NO: 8) | | |

α-Helical peptides based on sulfhydryl modification strategy and their molecular weights

| Number of Repeat Units (n) | Cysteine/Methionine Modification(s) | Peptide Sequence | Theoretical Mw | Measured Mw* |
|---|---|---|---|---|
| 2 | 1 | LLKKLLKKC-NH$_2$ (SEQ ID NO: 9) | 1085.51 | 1087.23 |
| | 2 | CLLKKLLKKC-NH$_2$ (SEQ ID NO: 10) | 1188.66 | 1190.11 |
| | 2 | MLLKKLLKKM-NH$_2$ (SEQ ID NO: 11) | 1244.76 | 1246.39 |
| 3 | 1 | LLKKLLKKLLKKC-NH$_2$ (SEQ ID NO: 12) | 1568.18 | 1569.25 |
| | 2 | CLLKKLLKKLLKKC-NH$_2$ (SEQ ID NO: 13) | 1671.32 | 1672.71 |
| | 2 | MLLKKLLKKLLKKM-NH$_2$ (SEQ ID NO: 14) | 1727.43 | 1729.16 |

*Measured by MALDI-TOF, apparent Mw = [Mw + H]$^+$

Circular Dichroism (CD) Spectroscopic Studies

Figure 1:
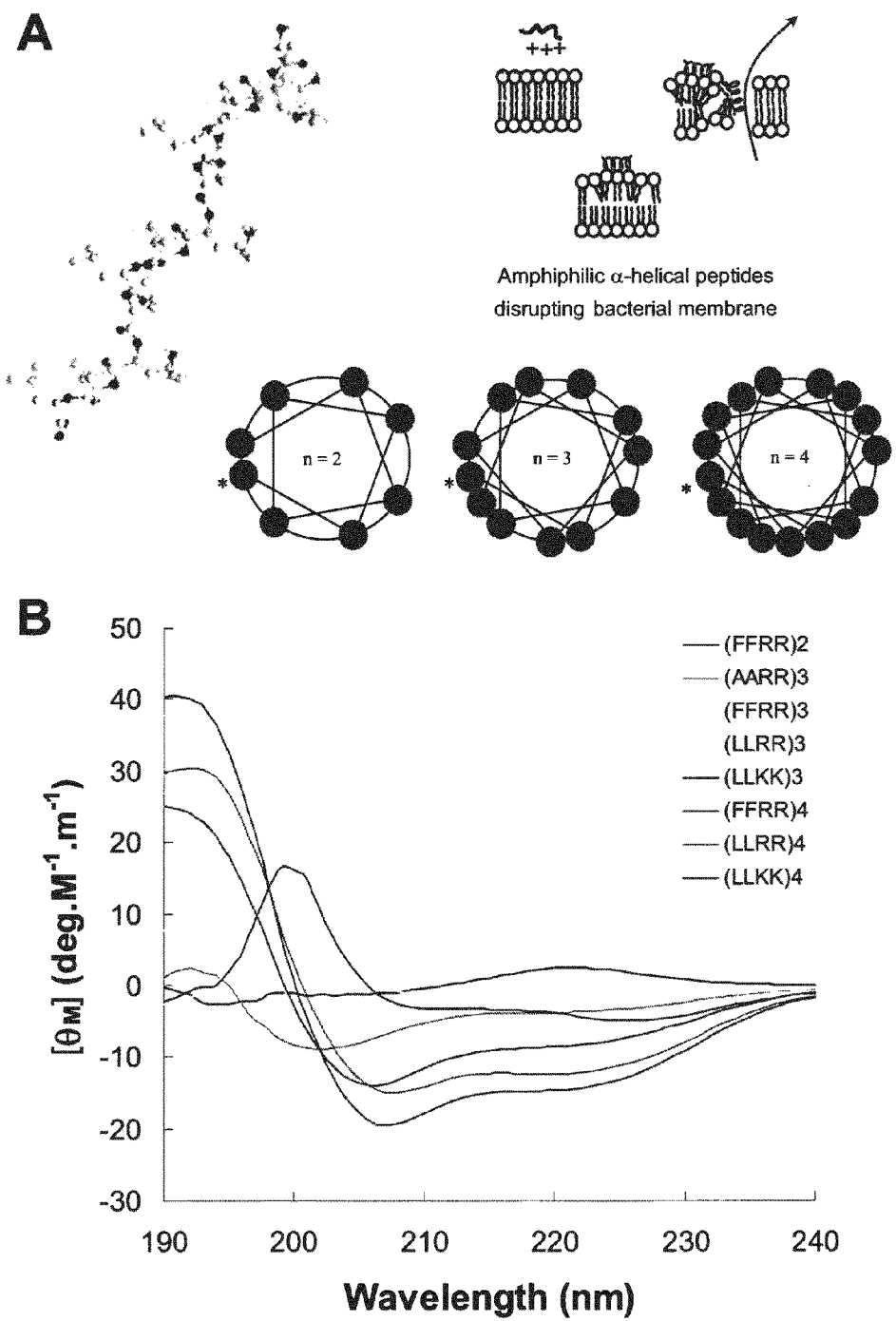
FIG. 1 shows a scheme illustrating the principle underlying the design of the synthetic α-helical peptides according to the present invention (A) and the CD-spectra of exemplary antimicrobial peptides in 25 mM SDS micelles; SEQ ID NOs: 1, 3, 2, 4, 5, 6, 7, and 8 can be found in the legend from top to bottom, respectively (B)

Most of the previously reported natural amphiphilic antimicrobial peptides adopt flexible random structure in aqueous solutions and assemble into a more rigid α-helical structure in the presence of a simulated membrane environment. SDS micelles can be used as a model lipid system because a similar detergent like SDS molecules had been reported to form micellar rings around the transmembrane helical region of a membrane protein, which were similar to the structure of the natural bilayer membrane. In order to investigate the proclivity of the conformational structures of the peptides in both water and membrane-like environments, they were first tested with CD spectroscopy technique at room temperature, by using both water and aqueous SDS micelle solution as the solvent. When water was used as the solvating medium, none of the peptides adopted any α-helical conformations (data not shown), while in the membrane-mimicking environment (i.e. in water containing SDS micelles), most of the peptides tested assembled into an α-helical conformation (FIG. 1). It is hypothesized that the cationic residues of the peptides initiate the association of the peptides onto the surface of SDS micelles through electrostatic interaction, which then allows the folding of the peptides to occur. It can be seen that both the composition and the length of the peptides affected the helicity of the peptide conformation (FIG. 1B). Peptides having phenylalanine as the hydrophobic residues did not show strong signal of α-helical secondary structure in solution, which was characterized by the presence of double minima at 220 nm and 208 nm UV-visible wavelengths. In contrast, peptides having leucine and lysine amino acid residues were found to exhibit strong α-helical signals. By comparing the molecular residual ellipticity, $[-\theta_M]$ values of the peptides at these wavelengths, the propensity of the peptides in forming α-helical confirmation could be arranged according to the order of (FFRR)$_2$ (SEQ ID NO: 1), (FFRR)$_3$ (SEQ ID NO: 2), (LLRR)$_3$ (SEQ ID NO: 4), (AARR)$_3$ (SEQ ID NO: 3), (FFRR)$_4$ (SEQ ID NO: 6), (LLKK)$_3$ (SEQ ID NO: 5), (LLRR)$_4$ (SEQ ID NO: 7), and (LLKK)$_4$ (SEQ ID NO: 8), from the weakest to the strongest inclinations. This observation is in agreement with the widely accepted knowledge of protein folding inclination that alanine, lysine and leucine residues have a stronger propensity of α-helical formation, while both phenylalanine and arginine residues have an indifferent propensity for such conformations. As such, peptides containing amino acids having weaker propensities to form helical structure required more repeat units to give typical α-helical CD spectra. In addition, peptides with more repeat units were also observed to form the α-helical structures more readily when compared to the shorter peptides, as implied by lower minimum value of the molecular elipiticy, $[-\theta_M]$, at 222 nm wavelength, which has been referenced as a measure of helical fraction of proteins in solution.

Hemolytic Activity of Peptides

As the peptides according to the present invention are also aimed for the purpose of biomedical applications in fighting against infectious disease, it is important to evaluate the extent of undesirable cytotoxic effect of the peptides. In the context of antimicrobial agents, cytotoxic effect is generally tested by analyzing the hemolytic properties of the antibiotics against mammalian red blood cells. Table 2A summarizes the peptide concentrations that resulted in 50% lysis of red blood cells (HC$_{50}$), which were estimated from the hemolysis tests of the peptides across a range of peptide concentrations as plotted in FIG. 2A. It is desirable that the HC$_{50}$ value of the peptides are as far away as possible from the effective antimicrobial concentration (listed in the same table). By comparing the HC$_{50}$ values of the different peptides, it is apparent that the hemolytic property of the peptides is affected by both the number of repeat units (length of peptides), and the nature of hydrophobic/cationic residues of the peptides. In general, peptides having 2 and 3 repeat units were not hemolytic up to 500 mg/L (the highest concentrations tested in this study), while the peptides having 4 repeat units were highly hemolytic (>60% hemolytic) even at low concentration of 31 mg/L (FIG. 2A). In this view, more repeat units seem to possess greater ability of penetrating and/or disrupting cell membrane owing to the increased hydrophobicity of the longer peptide molecule, hence exhibiting an increased hemolytic property. In addition, in view of providing free sulfhydryl/thioether groups for bacterial membrane lysis, one of the peptides having the highest tendency to fold into an α-helical conformation, (LLKK)$_n$ (SEQ ID NO: 18), was modified by attaching cysteine/methionine residue(s) at one or both termini of the peptides, followed by the analysis of their corresponding hemolytic properties. The HC$_{50}$ values of these modified peptides are summarized in Table 2B and FIG. 2B. As can be seen, comparison between the HC$_{50}$ of (LLKK)$_3$ (SEQ ID NO: 5) to (LLKK)$_3$C (SEQ ID NO: 12) and C(LLKK)$_3$C (SEQ ID NO: 13) infers that the hemolytic value was increased dramatically.

TABLE 2A

Minimum inhibitory concentrations (MIC) and 50% hemolytic concentrations (HC$_{50}$) of the synthetic α-helical antimicrobial peptides

| Antimicrobial Peptides | Peptide Sequence | MIC (mg/L) | | | HC$_{50}$ (mg/L) |
| --- | --- | --- | --- | --- | --- |
| | | B. subtilis | E. coli | C. albicans | |
| (FFRR)$_2$ (SEQ ID NO: 1) | FFRRFFRR-NH$_2$ (SEQ ID NO: 1) | 125 | >500 | >500 | >500 |
| (FFRR)$_3$ (SEQ ID NO: 2) | FFRRFFRRFFRR-NH$_2$ (SEQ ID NO: 2) | 31.3 | >500 | 125 | >500 |
| (AARR)$_3$ (SEQ ID NO: 3) | AARRAARRAARR-NH$_2$ (SEQ ID NO: 3) | >500 | >500 | >500 | >500 |
| (LLRR)$_3$ (SEQ ID NO: 4) | LLRRLLRRLLRR-NH$_2$ (SEQ ID NO: 4) | 15.6 | >500 | 500 | >500 |
| (LLKK)$_3$ (SEQ ID NO: 5) | LLKKLLKKLLKK-NH$_2$ (SEQ ID NO: 5) | 31.3 | >500 | 125 | >500 |
| (FFRR)$_4$ (SEQ ID NO: 6) | FFRRFFRRFFRRFFRR-NH$_2$ (SEQ ID NO: 6) | 20 | >50 | >50 | ~26 |
| (LLRR)$_4$ (SEQ ID NO: 7) | LLRRLLRRLLRRLLRR-NH$_2$ (SEQ ID NO: 7) | 10 | >50 | >50 | ~12 |
| (LLKK)$_4$ (SEQ ID NO: 8) | LLKKLLKKLLKKLLKK-NH$_2$ (SEQ ID NO: 8) | 10 | >50 | >50 | ~24 |

TABLE 2B

Minimum inhibitory concentrations (MIC) and 50% hemolytic concentrations (HC$_{50}$) of the synthetic antimicrobial peptides with sulfhydryl modification(s)

| Cysteine/Methionine Modification(s) | Peptide Sequence | MIC (mg/L) | | | | HC$_{50}$ (mg/L) |
| --- | --- | --- | --- | --- | --- | --- |
| | | B. subtilis | E. coli | P. aeruginosa | C. albicans | |
| 1 Cys, n = 2 | LLKKLLKKC-NH$_2$ (SEQ ID NO: 9) | 125 | >500 | 63 | 250 | >2500 |
| 2 Cys, n = 2 | CLLKKLLKKC-NH$_2$ (SEQ ID NO: 10) | 125 | 225 | 125 | 250 | >2500 |
| 2 Met, n = 2 | MLLKKLLKKM-NH$_2$ (SEQ ID NO: 11) | 125 | >500 | 500 | 500 | >2500 |
| 1 Cys, n = 3 | LLKKLLKKLLKKC-NH$_2$ (SEQ ID NO: 12) | 16 | 150 | 16 | 63 | ~402 |
| 2 Cys, n = 3 | CLLKKLLKKLLKKC-NH$_2$ (SEQ ID NO: 13) | 31 | 125 | 125 | 125 | ~82 |
| 2 Met, n = 3 | MLLKKLLKKLLKKM-NH$_2$ (SEQ ID NO: 14) | 31 | 250 | 31 | 125 | ~158 |

Minimum Inhibitory Concentrations (MIC) Measurements

All the exemplary peptides were tested for their MIC value against Gram-positive bacteria *B. subtilis*, and yeast *C. albicans* with a microdilution assay. Most of the peptides efficiently suppress these microbial cells at different effective concentration levels (see FIGS. 7 to 17). Table 2A summarizes the MIC values of exemplary peptides according to the present invention. Recalling the $HC_{50}$ values listed in the same table, most of the peptides with 3 repeat units have a MIC value lower than the $HC_{50}$ value, implying a wider therapeutic window, hence their potential usefulness as systemic antimicrobial agents. For example, (FFRR)$_3$ (SEQ ID NO: 2), (LLRR)$_3$ (SEQ ID NO: 4), and (LLKK)$_3$ (SEQ ID NO: 5) peptides had MIC values of 31.3, 15.6, and 31.3 mg/L against *B. subtilis* (Table 2A), respectively, and at these concentrations, less than 5% hemolysis was observed (i.e. less than 5% mammalian red blood cells were lysed) (FIG. 2A). On the other hand, for the yeast *C. albicans*, which is generally more difficult to kill, the MIC values were significantly increased as compared to that for *B. subtilis* (i.e., 125, 500, and 125 mg/L, respectively). At the MIC levels for *C. albicans*, these peptides induced 12-24% hemolysis, except for (LLKK)$_3$ (SEQ ID NO: 5) which induced only about 4.2% hemolysis (FIG. 2A). This suggests a good selectivity of these peptides towards the anionic constituent of microbial cell membranes, over the zwitterionic mammalian cell membranes. However, the (AARR)$_3$ (SEQ ID NO: 3) peptide was particularly ineffective against the microbial cells due to weak lipophilicity of the alanine residue, resulting in poor hydrophilicity/lipophilicity balance of the amphiphiles. In contrast to the peptides with 3 repeat units, peptides designed with 2 repeat units exhibited much weaker antimicrobial properties as it was only effective to inhibit the growth of *B. subtilis* at much higher concentration of 125 mg/L, but ineffective against *C. albicans* (Table 2A). Similarly, the peptides with 4 repeat units also exhibit much poorer selectivity towards bacterial cells over mammalian red blood cells, even though they were generally more effective to inhibit the growth of microbial cells at lower concentrations than those peptides with 3 repeat units. For example, (FFRR)$_4$ (SEQ ID NO: 2), (LLRR)$_4$ (SEQ ID NO: 4), and (LLKK)$_4$ (SEQ ID NO: 5) peptides have MIC values of 20, 10, and 10 mg/L against *B. subtilis* (Table 2A), respectively. However, at these concentrations, around 50%, 50%, and 30% of mammalian red blood cells were lysed (FIG. 2A). Presumably, such poorer selectivity was encountered due to the increased hydrophobicity and poorer facial amphiphilicity of these peptides. FIG. 1A shows the helical wheel schematic representation of the antimicrobial peptides according to the present invention for the 2, 3, and 4 repeat units peptides. It can be seen that the peptides with 3 repeat units resulted in the most "optimum" facially amphiphilic conformation, upon rearrangement into the corresponding α-helical secondary structures. In summary, among all the tested peptides, excellent selectivity over both *B. subtilis* and *C. albicans* was particularly demonstrated by the (LLKK)$_3$ (SEQ ID NO: 5) peptide, which could be due to a combination of proper hydrophobic-cationic balance, stronger inclination to form α-helical conformation in a membrane-like environment, as well as optimum facially amphiphilic helical conformation. Interestingly, further works on the modification of (LLKK)$_n$ (SEQ ID NO: 18) peptides family with 2 and 3 repeat units by cysteine modification yielded very good results. Table 2B summarizes the antimicrobial properties of this AMP family. It is shown that the spectrum of the antimicrobial activity of the peptides was enhanced by introducing a free sulfhydryl moiety to the terminal ends of the AMP. (XXYY)$_n$ peptides, which generally only show effective microbial inhibitive effects towards Gram-positive *B. subtilis* and yeast *C. albicans* (Table 2A), can also effectively inhibit Gram-negative *E. coli* growth upon the addition of the free sulfhydryl/thioether group(s). A more remarkable potential is particularly shown for the C(LLKK)$_2$C (SEQ ID NO: 10) peptide, which shows broad spectrum of antimicrobial effects at concentrations more than 10× lower than the corresponding $HC_{50}$.

Antimicrobial Mechanism

Figure 3:
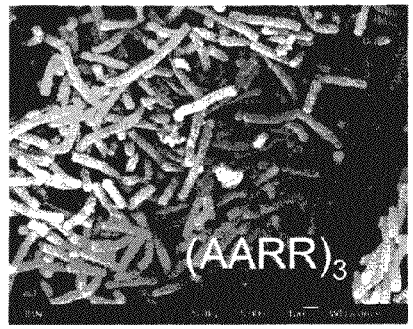
Figure 3:
Figure 3:
Figure 3:
Figure 3:
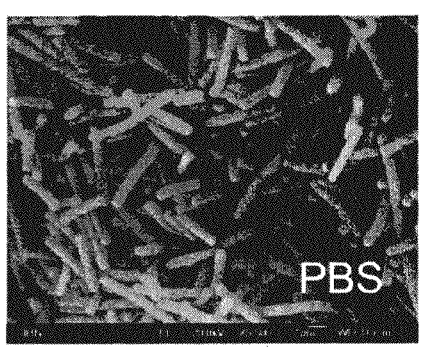
Figure 3:
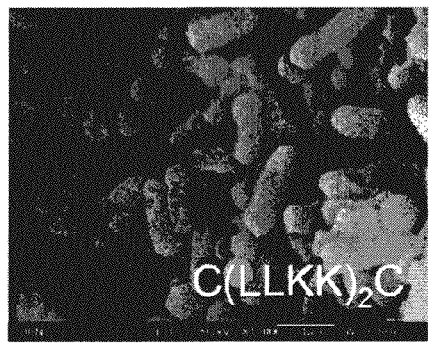
Figure 3:
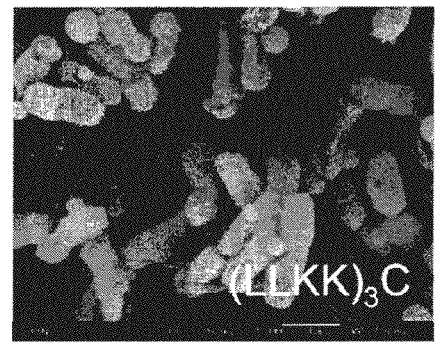
Figure 3:
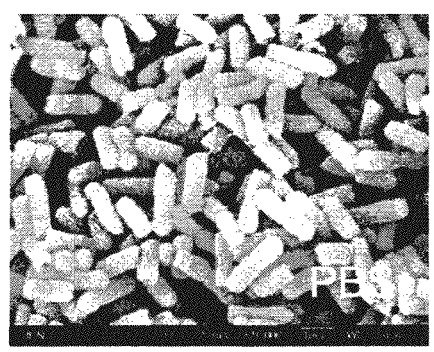

Based on the MIC and $HC_{50}$ values of the peptides, the potential use of the peptides with 3 repeat units in medical applications is more apparent than that of the others. Hence, these peptides were further studied in their antimicrobial actions in killing microbial cells by observing the integrity of bacterial cell membranes upon treatment with these peptides. FIG. 3 shows SEM images of *B. subtilis*, which were treated with different peptides of 3 repeat units at a concentration of 50 mg/L (above their corresponding MIC, except for (AARR)$_3$ (SEQ ID NO: 3) peptide) for 2 hours, and observed under FE-SEM after drying. As can be seen from these images, the treatment with most of the peptides induced a significant membrane damaging effect, in comparison to that with PBS as the negative control. In addition, the treatment with (AARR)$_3$ (SEQ ID NO: 3), which were not effective to inhibit the growth of *B. subtilis*, was observed to result in minimal membrane damage in minor population of the bacteria. The kinetics of the antimicrobial effect of the most selective and effective peptide in this study, (LLKK)$_3$ (SEQ ID NO: 5), was further studied qualitatively by observing the membrane structure of *B. subtilis* treated with the peptide for various time length. As shown in FIG. 4, it was observed that even for the short treatment of 10 minutes with the antimicrobial peptide (LLKK)$_3$ (SEQ ID NO: 5), a significant extent of membrane damage on some of the bacterial cells was observed.

In Vitro Immunogenicity Test

One important aspect of biomaterial development other than its functionality is its biocompatibility, which entails a long list of material properties as a reaction upon contact with biological tissues. Some of these properties include both cytotoxic as well as immunogenic aspects. Even though some studies arguably reported that it might be useful to have an antimicrobial peptide that could induce immunogenic response by the host organism via the Toll-like Receptor (TLR) pathways, in view of providing synergy for its microbial invasion clearance [6], an uncontrolled non-specific immunogenic response can become detrimental towards the host organism. In fact, such response may, under more severe conditions, result in a medical condition termed as hypercytokinemia or cytokinestorm, causing further severe inflammations.

Thus, the activity of the (LLKK)$_3$ (SEQ ID NO: 5) peptide, which is the most effective and selective in killing microbial cells, in inducing non-specific immunogenic response in vitro through the cytokine pathways was analyzed, by measuring the level of IFN-α and IFN-γ secretion (the two upstream cytokine signaling molecules that are involved in the immune system) by human PBMCs upon stimulation by the peptides. As summarized in FIG. 5, the secretion of these two cytokines was relatively low upon stimulation with the peptide, which is practically occurring at the basal-secretion level of the non-stimulated PBMCs. Furthermore, to ensure the validity of the test, the capability of the PBMCs to secrete these two cytokines was also demonstrated by a positive control group, at which PBMCs were stimulated with a highly immunogenic lipopolysaccharide.

SUMMARY

The present inventors have come up with a novel approach to design antimicrobial peptides based on the principles of α-helical peptide/protein folding theory. A series of synthetic antimicrobial peptides have been synthesized and evaluated for their efficacy against Gram-positive bacteria and yeast. These peptides are unfolded in a random structure in aqueous solution, but folded into α-helical structure upon interacting with a membrane environment. Peptides with more repeat units formed the α-helical structure more readily than the shorter peptides. An increased number of repeat units led to stronger antimicrobial activities and a higher degree of hemolysis. The peptides with 3 repeat units such as (FFRR)$_3$ (SEQ ID NO: 2), (LLRR)$_3$ (SEQ ID NO: 4), and (LLKK)$_3$ (SEQ ID NO: 5) had low MIC values, yet induced insignificant hemolysis. In particular, (LLKK)$_3$ (SEQ ID NO: 5) peptide had MIC values of 31.3 and 125 mg/L against *B. subtilis* and *C. albicans* respectively. At these concentrations, it caused less than 5% hemolysis. At a concentration slightly above its MIC, the peptide was shown to damage the membrane of *B. subtilis* as soon as 10 minutes after start of the incubation. This antimicrobial peptide did not induce non-specific immunogenicity in vitro via the IFN-α and IFN-γ pathways. Moreover, it has also been shown that addition of free sulfhydryl/thioether containing amino acid residue(s) at the termini of the peptides could enhance both the antimicrobial activity and spectrum. In particular, the peptide with 2 repeat units and modified at both ends, C(LLKK)$_2$C (SEQ ID NO: 10), exhibited antimicrobial activities against Gram-positive *B. subtilis*, Gram-negative *E. coli*, as well as yeast *C. albicans* at concentrations much lower than the corresponding HC$_{50}$ values. All these findings demonstrate that the peptides according to the present invention are promising antimicrobial agents against Gram-positive bacteria, Gram-negative bacteria, or yeast.

2. Branched and Star-Like Antimicrobial Peptides
2.1 Material and Methods
Peptide Synthesis, Conjugation and Characterization Amidated linear (LLKK)$_4$ (SEQ ID NO: 8) (LLKKLLKKLLKKLLKK-CONH$_2$; SEQ ID NO: 8) and 2-arm branched [(LLKK)$_2$]$_2$ ([LLKKLLKK]$_2$K*C—CONH$_2$) peptides were synthesized by GL Biochem (Shanghai, China), and the purity was characterized to be >95% through High Pressure Liquid Chromatography (HPLC). The star-like [(LLKK)$_2$]$_4$ peptide ([LLKKLLKK]$_2$K*C—$_S$—$_S$—CK*[KKLLKKLL]$_2$) was obtained as the product of oxidative dimerization of [(LLKK)$_2$]$_2$ molecules by forming disulfide bond between two thiol groups. Dimerization was conducted at 60-65° C. overnight in DMSO. The reaction mixture was purified with reverse phase HPLC, and 95% purity was achieved. The molecular weights of all the three peptides were measured with MALDI TOF/TOF (Autoflex II, Bruker Daltonics, U.S.A), and were reported as [Mw+H]$^+$ in FIG. 18A. The asterisk * indicates a branching point whereby the 1° amino group on the lysine's side chain was used for the incoming amino acid attachment. This branching point was introduced using Fmoc-Lys-Fmoc derivative during the solid-phase peptide synthesis, adapted from the peptide dendrimer synthesis strategy.

Differential Scanning Calorimetry (DSC)

Thermal analysis of the peptides was carried out to probe molecular rigidity/flexibility, as implied by the difference in Tg (glass transition temperature). Dried peptide (2-3 mg) was prepared in a sealed calorimetry pan and analyzed using a TA differential scanning calorimeter Q100 with +1° C. modulation every 60 s. Tg was determined from the second scan at a heating rate of 3° C./min following a slow cooling rate of 3° C./min to remove the influence of thermal history.

Circular Dichroism (CD) Spectroscopy

Secondary structure of the (LLKK)$_4$ (SEQ ID NO: 8), [(LLKK)$_2$]$_2$, and [(LLKK)$_2$]$_4$ peptides was analyzed in the presence of 25 mM SDS micelles as mimic of bacterial membrane. Briefly, peptides were prepared at 250 μM (in 25 mM SDS solution), and scanned with a CD spectropolarimeter (JASCO, J-810) at room temperature using 1.0 mm path length quartz cell. The CD spectra of the peptide solutions were acquired after solvent subtraction from 190 to 240 nm wavelengths at 50 nm/min scanning speed. 10 runs were performed for each peptide to reduce random noise on the background. The acquired CD spectra were converted into the mean residue of ellipticity by using the following equation:

$$\theta_M = \frac{\theta_{obs}}{10} \cdot \frac{M_{RW}}{c \cdot l}$$

where $\theta_M$ is the residue of ellipticity [deg·M$^{-1}$·m$^{-1}$], $\theta_{obs}$ is the observed ellipticity corrected for the buffer at a given wavelength [mdeg]. $M_{RW}$ is residue molecular weight, defined as Mw/number of amino acids), and c is the peptide concentration [mg/mL], and l is the path length [cm].

Hemolytic Activity

The peptides' hemolysis was tested in human red blood cells (hRBC). hRBCs were diluted 25× to achieve 4% concentration (v %) in phosphate-buffered saline (PBS, pH 7.4). Upon dilution, the blood suspension was treated with equal volume of (LLKK)$_4$ (SEQ ID NO: 8), [(LLKK)$_2$]$_2$, or [(LLKK)$_2$]$_4$ peptide solution in PBS to reach final peptide concentrations of 0-500 mg/L. The treatment was performed inside a 37° C. incubator for 1 hour, after which the mixture was centrifuged at 1000 g for 5 mins to remove the non-hemolysed blood cells. The supernatant (100 μL) was transferred into a 96-well plate, and measured spectrophotometrically for its absorbance at 567 nm using a microplate reader (TECAN, Switzerland)[5]. PBS and 0.1% Triton-X were used as negative and positive controls respectively. Hemolysis level was calculated according to the following formula:

% Hemolytic=(Absorbance for Peptide treatment−
 Absorbance for PBS treatment)/(Absorbance for
 Triton treatment−Absorbance for PBS treatment)×100%

Minimum Inhibitory Concentration (MIC)

The antimicrobial effect of (LLKK)$_4$ (SEQ ID NO: 8), [(LLKK)$_2$]$_2$, and [(LLKK)$_2$]$_4$ peptides was tested according to the standardized broth microdilution technique against Gram-positive bacteria *B. subtilis* (ATCC No. 23857), and *S. aureus* (ATCC No. 29737), Gram-negative bacteria *E. coli* (ATCC No. 25922), *E. aerogenes* (ATCC No. 13048) and *P. aeruginosa* (ATCC No. 9027), as well as Yeast *C. albicans* (ATCC No. 10231). Microbes were re-constituted from their dried pellets obtained from ATCC according to the recommended protocols. Bacterial culture was done in tryptic soy broth at 37° C., while yeast was cultured in yeast mould broth at room temperature, under constant shaking at 100 rpm. Briefly, microbial suspension was first adjusted to contain ~3×10$^8$ CFU/mL, by adjusting its 600 nm absorbance to be equivalent to that of the standard McFarland 1 reference. The suspension was then diluted to contain ~3×10$^6$ CFU/mL. Under this condition, the O.D. reading was approximately 0.05-0.06 for bacterial cultures, and 0.03-0.04 for yeast cultures. Equal volume (100 μL) of the microbial suspension and the peptide solutions was mixed in a 96-well plate, and the microbial growth was monitored by measuring the O.D. reading at 0 and 18 hours. The test was conducted for concentrations of 0-50 mg/L for (LLKK)$_4$ (SEQ ID NO: 8) peptide, and 0-500 mg/L for [(LLKK)$_2$]$_2$ and [(LLKK)$_2$]$_4$ peptides, because the linear peptide is highly hemolytic. MIC was reported as the minimum concentration required for inhibiting the growth of microbial cells after 18 hours of incubation.

Scanning Electron Microscopy (SEM) Imaging

*E. coli* and *S. aureus* at ~3×10$^8$ CFU/mL were treated with 250 mg/L star-like [(LLKK)$_2$]$_4$ peptide (equal volume) for 1 hr, after which, the samples were dehydrated and dried as described above.

Disk Diffusion Assay (DDA)

Approximately 3×10$^8$ CFU/mL microbial suspensions (*B. subtilis, C. albicans, E. coli, E. aerogenes, P. aeruginosa*, and *S. aureus*) (20 μL each) were spread on 1.5% LB agarose plates and incubated for 24 hrs (for bacteria) or 48 hrs (for yeast). Disks were prepared to contain 50 μg of (LLKK)$_4$ (SEQ ID NO: 8) or 500 μg of [(LLKK)$_2$]$_2$ and [(LLKK)$_2$]$_4$ by dripping 50 μL of the corresponding peptide solutions onto a sterile disk. Different amounts of (LLKK)$_4$ (SEQ ID NO: 8), [(LLKK)$_2$]$_2$ and [(LLKK)$_2$]$_4$ peptides were used due to the difference in their hemolytic properties, and were kept consistent to the highest concentrations used at the MIC tests. Disks were air-dried for several minutes before being placed onto different zones in the agar plates.

Time-Killing Curve and Fractional Survival Tests

*E. coli* and *S. aureus* were treated at MIC and 2×MIC concentrations with [(LLKK)$_2$]$_4$ peptide. At various time periods (0, 0.5, 1, 2, 5, 8 and 18 hours), microbial suspensions were diluted at 3 different dilutions and plated on 1.5% LB agar plates. Microbial colonies were formed and counted after 24 hours of incubation (for bacteria) or 48 hours of incubation (for yeast).

perature (T$_g$) analysis (FIG. 18B). Analogous to the case for polymers, lower T$_g$ for the 2-arm [(LLKK)$_2$]$_2$ peptide suggested that its backbone was relatively less rigid compared to that of the linear (LLKK)$_4$ (SEQ ID NO: 8) peptide.

The effect of the structural design of peptide molecules on their helical folding behavior was further analyzed. FIG. 18C shows folding behavior of the peptides into α-helices upon interaction with SDS micelles used to mimic bacterial cell membrane. Generally, more repeat units enhance the helical propensity by virtue of enhanced hydrogen-bonding interaction along the helical backbone that stabilizes such helical structure. Therefore, it is intuitive that branching of the peptide into 2-arm and star-like structures, which "breaks" the overall length of the peptide backbone per arm, reduced the α-helical signals. In addition, the star-like [(LLKK)$_2$]$_4$ peptide displayed almost identical folding behavior as the 2-arm [(LLKK)$_2$]$_2$ peptide, which was plausibly due to the same helical length of each arm (i.e. the same number of amino acids forming each "arm" from the branching point to the terminal amino acid).

The undesired hemolytic activity of the peptides towards human red blood cells (hRBC) was assessed as shown in FIG. 18D. The linear peptide (LLKK)$_4$ (SEQ ID NO: 8), which was originally highly hemolytic even at low concentrations (e.q. 50% hemolysis at ~37.5 mg/L), became much less hemolytic when a branching point was introduced into the molecule (i.e., 2-arm branched [(LLKK)$_2$]$_2$ peptide, only ~18% hemolysis at 500 mg/L). Furthermore, the star-like [(LLKK)$_2$]$_4$ peptide was also only hemolytic at an acceptable level, in comparison to its antimicrobial activities towards a wide spectrum of microbial families (Table 3). This was possibly because of increased flexibility and reduced helical propensity of peptide molecules after branching (FIGS. 18B and 18C).

TABLE 3

Biological activities (MIC and HC50) of linear (LLKK)4 (SEQ ID NO: 8), 2-arm branched [(LLKK)2]2, and star-like [(LLKK)2]4 α-helical peptides.

| | MIC [mg/L] | | | | | | |
|---|---|---|---|---|---|---|---|
| Peptide | B. subtilis | S. aureus | E. coli | E. aerogenes | P. aeruginosa | C. albicans | HC50 [mg/L] |
| (LLKK)$_4$ (SEQ ID NO: 8) | 6.3 | >50 | 12.5 | 25 | 6.3 | >50 | ~37.5 |
| [(LLKK)$_2$]$_2$ | 8 | >500 | 31 | 125 | 8 | 63 | >500 |
| [(LLKK)$_2$]$_4$ | 16 | 400 | 16 | 63 | 8 | 125 | >500 |

2.2 Results

A branch point was introduced at the center of a linear (LLKK)$_4$ (SEQ ID NO: 8) peptide to form 2 arms of (LLKK)$_2$ (SEQ ID NO: 19) connected via a KC dipeptide (i.e. a 2-arm branched [(LLKK)$_2$]$_2$ peptide), in order to introduce flexibility into this helical molecule. The KC dipeptide served as a flexible bending point within the 2-arm [(LLKK)$_2$]$_2$ molecule to reduce its overall rigidity. In addition, the presence of cysteine residue at the C-terminal end of the peptide [(LLKK)$_2$]$_2$ provided a thiol group for intermolecular dimerization into a star-like [(LLKK)$_2$]$_4$ peptide based on thermal oxidation as confirmed by MALDI-TOF/TOF analysis (FIG. 18A). In order to probe the flexibility/rigidity difference between the linear and branched peptide, glass transition thermal analysis was conducted. Since the linear (LLKK)$_4$ (SEQ ID NO: 8) and 2-arm branched [(LLKK)$_2$]$_2$ peptides had comparable molecular weight, their relative flexibility/rigidity of the molecular chain could be probed by glass transition tem- Next, the biological activity and selectivity of these peptides were evaluated by measuring their minimum inhibitory concentrations (MICs) against a wide range of microbial cells including clinically important microbes, i.e., *B. subtilis, S. aureus* (Gram-positive), *E. coli, E. aerogenes, P. aeruginosa* (Gram-negative), and *C. albicans* (yeast) (FIGS. 21 to 26). As listed in Table 1, the linear (LLKK)$_4$ (SEQ ID NO: 8) peptide was efficient against most microbes tested except for *S. aureus* and *C. albicans*. However, it caused significant hemolysis at concentrations around its MICs. Branching of the helical peptide structure gave rise to higher MIC values (2-arm [(LLKK)$_2$]$_2$ versus (LLKK)$_4$ (SEQ ID NO: 8) in Table 3), whereas selectivity (defined as HC$_{50}$/MIC) of the branched peptide towards microbes was significantly increased. For example, selectivity of the peptides towards *E. coli* was ~3 for the linear (LLKK)$_4$ (SEQ ID NO: 8) peptide, and >16.1 for the 2-arm [(LLKK)$_2$]$_2$ peptide, respectively (Table 4).

TABLE 4

Selectivity (HC$_{50}$/MIC) of linear (LLKK)$_4$ (SEQ ID NO: 8), 2-arm branched [(LLKK)$_2$]$_2$, and star-like [(LLKK)$_2$]$_4$ α-helical peptides.

| Peptide | Selectivity (HC$_{50}$/MIC) | | | | | |
|---|---|---|---|---|---|---|
| | B. subtilis | S. aureus | E. coli | E. aerogenes | P. aeruginosa | C. albicans |
| (LLKK)$_4$ (SEQ ID NO: 8) | 6 | N/A | 3 | 1.5 | 6 | N/A |
| [(LLKK)$_2$]$_2$ | >62.5 | N/A | >16.1 | >4 | >62.5 | >7.9 |
| [(LLKK)$_2$]$_4$ | >31.3 | >1.3 | >31.3 | >7.9 | >62.5 | >4 |

Further increasing branching degree without disturbing the cationic-hydrophobic balance (star-like [(LLKK)$_2$]$_4$ versus 2-arm [(LLKK)$_2$]$_2$) enhanced antimicrobial potency and improved microbial selectivity for the majority of the microbes tested. For example, compared to the 2-arm [(LLKK)$_2$]$_2$ peptide, MIC of the star-like [(LLKK)$_2$]$_4$ peptide against *E. coli* was lower with higher selectivity (MIC: 16 versus 31 mg/L; Selectivity: >31.3 versus >16.1) (Table 3 and Table 4).

The activity of the peptides in preventing colony formation of the microbial cells was also studied qualitatively with a disk diffusion assay (DDA) technique. Microbes (*B. subtilis, S. aureus, E. coli, E. aerogenes, P. aeruginosa* and *C. albicans*) were plated on agar plates at ~10$^8$ CFU/mL (20 μL) microbial suspension, and sterile disks (1: growth medium, 2: linear (LLKK)$_4$ (SEQ ID NO: 8) peptide at 50 μg/disk, 3: 2-arm [(LLKK)$_2$]$_2$ peptide at 500 μg/disk, 4: star-like [(LLKK)$_2$]$_4$ peptide at 500 μg/disk) were placed accordingly on the agar plates. Different concentration between disk 2, 3 and 4 was to account for the hemolytic properties of linear (LLKK)$_4$ (SEQ ID NO: 8) peptide and MIC values of the peptides (incubation time: 24 hours for bacteria and 48 hours for yeast). As shown in FIG. 19, both the 2-arm and star-like peptides had higher activity to prevent colony formation of all types of microbes tested on the agar plates, by virtue of the observable zone of inhibition around the disk containing these two peptides. Based on the hemolytic and antimicrobial activity results, the star-like peptide was the best among the three peptides tested. Therefore, the capability of the star-like peptide in killing bacterial cells was further investigated by analyzing the fractional cell survival upon peptide treatment at MIC and 2×MIC concentrations at various exposure times. For this purpose, Gram-negative *E. coli* and Gram-positive *S. aureus* were chosen as the model microorganisms; as shown in FIG. 20A, more than 50% of the cells were killed after exposure to the peptide for 1 hour at MIC or 2×MIC concentrations. At the prolonged incubation time of 8 hours, the star-like peptide at both concentrations could kill more than 99.99% of the bacterial cells. Furthermore, the CFU counts at 18 hours of incubation (FIG. 27) revealed that the peptide killed bacterial cells with at least 6 log reduction killing efficiency at MIC concentration, while more than 11 log reduction killing efficiency was observed at 2×MIC concentration. The antimicrobial function of the star-like [(LLKK)$_2$]$_4$ peptide via disrupting Gram-negative *E. coli* and Gram-positive *S. aureus* cell membranes was further confirmed via SEM imaging shown in FIG. 20B.

REFERENCES

[1] Zasloff M. Antimicrobial peptides of multicellular organisms. Nature 2002; 415:389-395.
[2] Wang Z, Wang G. APD: the antimicrobial peptide database. Nucleic Acids Res 2004; 32:590-592.
[3] Ulvatne H, Vorland L H. Bactericidal kinetics of 3 lactoferrins against *Staphylococcus aureus* and *Escherichia coli*. Scand J Infect Dis 2001; 33:507-511.
[4] Diekema D J, Bootsmiller B J, Vaughn T E, Woolson R F, Yankey J W, Ernst E J, et al. Antimicrobial resistance trends and outbreak frequency in United States hospitals. Clin Infect Dis 2004; 38:78-85.
[5] Hancock R E, Patrzykat A. Clinical development of cationic antimicrobial peptides: from natural to novel antibiotics. Curr Drug Targets Infect Disord 2002; 2:79-83.
[6] Hancock R E, Sahl H G. Antimicrobial and host-defense peptides as new anti-infective therapeutic strategies. Nat Biotechnol 2006; 24:1551-1557.

The invention claimed is:

1. A peptide consisting of a general formula selected from the group consisting of

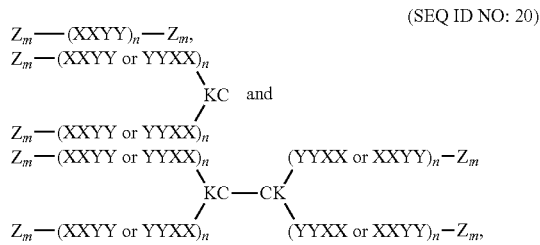
(SEQ ID NO: 20)

wherein
- X is, at each occurrence, independently selected from the group consisting of leucine (L), isoleucine (I), valine (V) and phenylalanine (F);
- Y is, at each occurrence, independently selected from the group consisting of lysine (K) and arginine (R);
- Z is selected from the group consisting of cysteine (C) and methionine (M);
- n is an integer number between 2 and 4; and
- m is, at each occurrence, independently selected from 0 and 1, and wherein each C-terminus of said peptide is amidated.

2. The peptide of claim 1, wherein said peptide is selected from the group consisting of (LLKK)$_3$ (SEQ ID NO: 5), (FFRR)$_2$ (SEQ ID NO: 1), (FFRR)$_3$ (SEQ ID NO: 2), (LLRR)$_3$ (SEQ ID NO: 4), (FFRR)$_4$ (SEQ ID NO: 6), (LLRR)$_4$ (SEQ ID NO: 7), (LLKK)$_2$C (SEQ ID NO: 9), C(LLKK)$_2$C (SEQ ID NO: 10), M(LLKK)$_2$M (SEQ ID NO: 11), (LLKK)$_3$C (SEQ ID NO: 12), C(LLKK)$_3$C (SEQ ID NO: 13) and M(LLKK)$_3$M (SEQ ID NO: 14).

3. A pharmaceutical composition comprising the peptide of claim 2.

4. A method of lysing a bacterial, yeast or fungal cell, said method comprising the step of exposing said cell to the peptide of claim 2.

5. A kit comprising the peptide of claim 2.

6. The peptide of claim 1, wherein said peptide is selected from the group consisting of

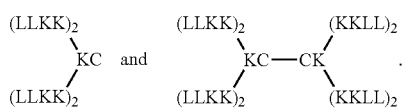

7. A pharmaceutical composition comprising the peptide of claim 6.

8. A method of lysing a bacterial, yeast or fungal cell, said method comprising the step of exposing said cell to the peptide of claim 6.

9. A kit comprising the peptide of claim 6.

10. A pharmaceutical composition comprising the peptide of claim 1.

11. A method of lysing a bacterial, yeast or fungal cell, said method comprising the step of exposing said cell to the peptide of claim 1.

12. A kit comprising the peptide of claim 1.

13. The peptide of claim 1, wherein n is 2 or 3.

* * * * *